(12) United States Patent
Lim et al.

(10) Patent No.: US 7,226,487 B2
(45) Date of Patent: Jun. 5, 2007

(54) 2-(AMINO OR SUBSTITUTED AMINO)-5-(SUBSTITUTED OXYMETHYL)-PHENOL COMPOUNDS, DYEING COMPOSITIONS CONTAINING THEM, AND USE THEREOF

(75) Inventors: Muill Lim, West Chester, OH (US); Robert Wayne Glenn, Virginia Water (GB); Andrew A Paul, Virginia Water (GB); Philip David Bolton, Teddington (GB)

(73) Assignee: The Procter & Gamble Company, Cincinnati, OH (US)

( * ) Notice: Subject to any disclaimer, the term of this patent is extended or adjusted under 35 U.S.C. 154(b) by 275 days.

(21) Appl. No.: 10/884,770

(22) Filed: Jul. 2, 2004

(65) Prior Publication Data
US 2005/0005370 A1    Jan. 13, 2005

Related U.S. Application Data

(60) Provisional application No. 60/485,264, filed on Jul. 7, 2003.

(51) Int. Cl.
*A61K 7/13* (2006.01)
(52) U.S. Cl. ............... 8/405; 8/406; 8/408; 8/410; 8/411; 8/412; 8/416; 8/421; 8/424; 8/435
(58) Field of Classification Search ............ 8/405, 8/406, 408, 410, 411, 412, 416, 421, 424, 8/435
See application file for complete search history.

(56) References Cited

U.S. PATENT DOCUMENTS

| | | | |
|---|---|---|---|
| 4,396,392 A | 8/1983 | Konrad | |
| 4,396,710 A | 8/1983 | Bergthaller | |
| 4,567,272 A | 1/1986 | Orth | |
| 5,019,130 A | 5/1991 | Flood | |
| 5,120,637 A | 6/1992 | Furusawa | |
| 5,961,667 A * | 10/1999 | Doehling et al. ............ | 8/408 |
| 5,980,585 A | 11/1999 | Terranova | |
| 6,022,381 A * | 2/2000 | Dias et al. ................. | 8/406 |
| 6,248,137 B1 | 6/2001 | Terranova | |
| 6,730,789 B1 | 5/2004 | Birault | |
| 6,774,244 B2 | 8/2004 | Lim | |
| 2001/0023514 A1* | 9/2001 | Cottard et al. ............ | 8/406 |
| 2002/0032935 A1 | 3/2002 | Ohashi et al. | |
| 2002/0170124 A1 | 11/2002 | Lim | |

FOREIGN PATENT DOCUMENTS

| | | |
|---|---|---|
| DE | 3804221 A1 | 3/1989 |
| DE | 20206274 U1 | 9/2002 |
| JP | 63-045282 A | 2/1988 |
| JP | 63045282 A * | 2/1988 |
| JP | 06130603 | 5/1994 |
| JP | 3258713 | 2/2002 |
| WO | WO-02/058657 A1 | 8/2002 |

OTHER PUBLICATIONS

English Abstract of the Patent DE 20206274 U1.*
STIC Search Report.*
XP-002335822, Chemical Abstracts Service, Columbus, OH, Sudiyama, N., "2-Phenylcoumarone Derivatives. III. Synthesis of a New Dye, Dicoumarone Red 1 and 2,3-diarylcoumaronoqulnone" (Apr. 22, 2001).
XP-002335823, Chemical Abstracts Service, Columbus, OH, Greenlaigh, C.W., et al., "The Benzofuranone Chromogen and Its Application to Disperse Dyes" (Nov. 8, 1994).
XP-002335824, Chemical Abstracts Service, Columbus, OH, Sessler, J.L., et al., "Method for the Preparation of cyclo[n]pyrroles Via An Oxidative Coupling Procedure" Sep. 5, 2003).
XP-002335825, Chemical Abstracts Service, Columbus, OH, Dann, O., et al., "Polynuclear Thiophanas. IV. Thioopheno [2', 3', 5, 6]thianaphthene" (Apr. 22, 2001).

* cited by examiner

*Primary Examiner*—Eisa Elhilo
(74) *Attorney, Agent, or Firm*—Brian M. Bolam; Melissa G. Krasovec; Tara M. Rosnell

(57) ABSTRACT

Disclosed are 2-(amino or substituted amino)-5-(substituted oxymethyl)-phenol compounds according to the Formula (I), as defined herein. Also, compositions for the oxidative dyeing of keratin fibers, comprising a medium suitable for dyeing and a compound of the Formula (II), as defined herein. The substituents of both formulae may themselves be substituted or unsubstituted. Further, methods for oxidative dyeing of keratin fibers, comprising applying such compositions in the presence of an oxidizing agent, for a period which is sufficient to develop the desired coloration.

56 Claims, No Drawings

2-(AMINO OR SUBSTITUTED AMINO)-5-(SUBSTITUTED OXYMETHYL)-PHENOL COMPOUNDS, DYEING COMPOSITIONS CONTAINING THEM, AND USE THEREOF

CROSS REFERENCE TO RELATED APPLICATION

This application claims the benefit of U.S. Provisional Application No. 60/485,264, filed Jul. 7, 2003.

FIELD OF INVENTION

This invention relates to 2-(amino or substituted amino)-5-(substituted oxymethyl)-phenol compounds, compositions for the oxidative dyeing of keratin fibers (preferably hair) comprising such compounds, and use thereof.

BACKGROUND OF THE INVENTION

Dyeing of keratin fibers, particularly hair, is known. The desire to alter the color of hair is not a facet of modern times. Hair color is altered to accommodate changes in fashion, style, and personal preference. However, obtaining good coloring and wearability without undesirable side effects to the hair and skin, remains an elusive goal. A suitable method of coloring hair is through oxidative dyeing. A variety of colors may be obtained, including yellows. Although the inventors choose not to speculate on the veracity of the adage according to which reputedly "blondes have more fun," they do recognize that yellow dyes themselves are desired.

Yellow dyes, particularly those used in coloring hair, should provide good coloring, including intensity of coloration and/or fastness, and be able to perform in spite of external agents, such as light, particularly sunlight, adverse weather conditions, washing and styling, permanent waving, perspiration, and/or friction. Such dyes should also be favourable as to toxicology and dermatology. They should be useful in providing a wide range of shades when combined with other ingredients and process stages, too.

The use of 2-aminophenol (also known as ortho-aminophenol or OAP) and some derivatives thereof, for yellow dyeing of keratin is known. For example, U.S. Pat. No. 4,396,392 (Wella, AG) discloses 2-amino-5-methyl-phenol, WO 02/058,657 (Clairol, Inc.) discloses 2-(amino or amino substituted)-5-methyl-phenol, and DE 202,06,274U1 (Wella, A G) discloses 2,3-diaminophenol derivatives, each for use in providing yellow color, alone and in combination with other coloring agents.

However, many previous oxidative dye compounds and combinations of such compounds resulting in yellow colourations have demonstrated poor wearability and stability to light, and some have recently experienced objections to their use from a toxicological standpoint. OAP, in particular, has been found to provide poor yellow, e.g. with off-tones. One alternative approach has been to use direct non-oxidative dyes alone or in combination with lessened quantities of oxidative dyes. However, this approach has been found to result in poor wash fastness upon shampooing, among other undesirable effects. There remains a need to provide further oxidative dye alternatives to known dyes, preferably yellow dyes, and compositions for dyeing of hair comprising them, that produce good coloration, preferably a bright yellow colouration, that exhibit good dye uptake by the hair, are useful in providing shades or colors which are stable over a reasonable period of time, provide good wash fastness and wearability, good selectivity, do not undergo significant change on exposure to light, shampooing or acid perspiration, and/or exhibit a favourable safety profile.

Compounds according to the following formula are disclosed in JP 63-045,282 (Kanegafuchi Chem. Ind. Co.) as reagents for the synthesis of certain anti-microbial agents, however, not as oxidative dyes:

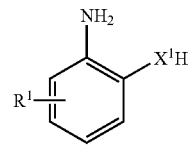

wherein $X^1$ is O or S; and wherein $R^1$ is selected from formyl, $C_1$ to $C_3$ alkyl substituted with a halogen atom, $C_1$ to $C_4$ acyl, —$(CH_2)_m X^2$ (wherein m is 1 to 4; $X^2$ is —OH, cyano, $C_1$ to $C_3$ alkoxy, tetrapyranyloxy, $C_1$ to $C_4$ acyl), and salts thereof, as defined therein.

The inventors have surprisingly found that by placing an oxymethyl group at the 5-position (5-oxymethyl) of a 2-(amino or substituted amino)-phenol, compounds exhibiting one or more of the aforementioned desirable qualities may be provided. Without being bound by theory, it is believed that the addition of such a hydrophilic side chain in this position may provide similar or greater coloration and/or wash fastness with improved toxicology versus previous 2-amino phenols and 2-amino phenol derivatives.

SUMMARY OF THE INVENTION

This invention relates to 2-(amino or substituted amino)-5-(substituted oxymethyl)-phenol compounds according to the Formula (I), as defined herein. The substituents may themselves be substituted or unsubstituted. This invention further relates to a composition for the oxidative dyeing of keratin fibers, comprising a medium suitable for dyeing and a compound of the Formula (II), as defined herein. This invention further relates to a method for oxidative dyeing of keratin fibers, comprising applying such compositions in the presence of an oxidizing agent, for a period sufficient to develop the desired coloration.

DETAILED DESCRIPTION OF THE INVENTION

All documents cited are, in relevant part, incorporated herein by reference; the citation of any document is not to be construed as an admission that it is prior art with respect to the present invention. The compositions of this invention can comprise, consist of, or consist essentially of the essential elements and limitations of the invention described herein. The components of the compositions of this invention, including those that may optionally be added, as well as methods for preparation, and methods for use thereof, and several exemplary embodiments are described in detail below. Except as otherwise noted, amounts represent approximate weight percent of the actual amount of the ingredient, and do not include solvents, fillers or other materials which may be combined with the ingredient in commercially available products, and the amounts include the composition in the form of intended use. Except as otherwise noted, all amounts including part, percentages, and proportions are understood to be modified by the word "about", and amounts are not intended to indicate significant digits. Except as otherwise noted, the articles "a", "an", and "the" mean "one or more".

As used herein, the term "hair" refers to keratinous fibers on a living, e.g. a person, or non-living body, e.g. in a wig, hairpiece, or other aggregation of non-living keratinous fibers. Mammalian, preferably human, hair is a preferred. Notably, hair, wool, fur, and other keratinous fibers are suitable substrates for coloring by the compounds and compositions described herein.

As used herein, the term "hair dyeing composition" refers to the composition containing one or more oxidation dyes, including the compounds described herein, prior to admixture with the developer composition. The term "developer composition" (which encompasses the term oxidizing agent composition) refers to compositions containing an oxidizing agent prior to admixture with the hair dyeing composition. The term "hair dyeing system" refers to the combination of the hair dyeing composition and the developer composition before admixture, and may further include a conditioner product and instructions, such product or system often being provided packaged as a kit. The term "hair dyeing product composition" refers to the composition formed by mixing the hair dyeing composition and the developer composition.

As used herein, "heteroalkyl" means a paraffinic (paraffin is also called alkane) hydrocarbon group containing at least one heteroatom (element other than carbon).

As used herein, "heteroaliphatic" means a group of organic compounds characterised by straight- or branched-chain arrangement of the constituent carbon comprising at least one heteroatom. Heteroaliphatics are comprised of three sub-groups: heteroalkanes, all of which are saturated; heteroalkenes, which are unsaturated; and heteroalkynes, which contain a triple bond. In complex structures the chains may be branched or cross-linked.

As used herein, "heteroolefinic" means a class of unsaturated hydrocarbons containing at least one heteroatom and having one of more double bonds. Those containing one double bond are called heteroalkenes, and those with two heteroalkadienes, or heterodiolefin. They are named after their corresponding paraffins by adding '-ene' or '-ylene' to the stem.

As used herein, "cosmetically acceptable" means that ingredients which the term describes are suitable for use in contact with the skin or hair of humans and lower animals without undue toxicity, incompatibility, instability, irritation, allergic response, and the like.

I. Compounds

The inventive compounds are compounds of the Formula (I), or its salts with an inorganic or organic acid:

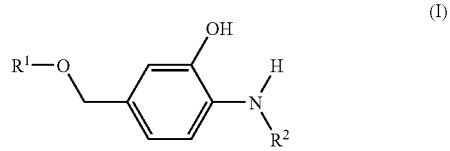
(I)

wherein $R^1$ is monovalent and is selected from: (a) substituted or unsubstituted, straight or branched, alkyl, mono- or poly-unsaturated alkyl, heteroalkyl, aliphatic, heteroaliphatic, or heteroolefinic systems, (b) substituted or unsubstituted, mono- or poly-cyclic aliphatic, aryl, or heterocyclic systems, or (c) substituted or unsubstituted, mono-, poly-, or per-fluoro alkyl systems; the systems of (a), (b) and (c) comprising from 1 to 12 carbon atoms and 0 to 5 heteroatoms selected from O, S, N, P, and Si; and wherein $R^2$ is monovalent and is selected from: (a), (b) and (c) herein, or H.

Without being bound by theory, it is believed that the presence of a divalent oxygen attached to the benzylic carbon in relation to the benzene ring, may provide similar or greater coloration and/or wash fastness with improved toxicology versus previous compounds. It is believed that compounds having such an arrangement may exhibit increased hydrophilicity, but without unduly adding an unfavourable increase in molecular weight that may interfere with the molecule's ability to penetrate the hair shaft. Compounds having such an arrangement are also believed to not adversely affect the ability to form a yellow chromophore in hair.

Preferably, $R^1$ is selected from: (a) substituted or unsubstituted, straight or branched, alkyl, heteroalkyl, aliphatic, heteroaliphatic, or heteroolefinic systems, (b) substituted or unsubstituted, mono- or poly-cyclic aliphatic, aryl, or heterocyclic systems, or (c) substituted or unsubstituted, mono-, poly-, or per-fluoro alkyl systems; more preferably (a) substituted or unsubstituted, straight or branched, alkyl, heteroalkyl, aliphatic, or heteroaliphatic systems, (b) substituted or unsubstituted, aryl, or heterocyclic systems, or (c) substituted or unsubstituted, mono-, poly-, or per-fluoro alkyl systems; more preferably substituted or unsubstituted, straight or branched, alkyl, or heteroalkyl systems.

Preferably, the preferred $R^1$ systems of (a), (b), and (c), described above, comprise from 1 to 8 carbon atoms and 0 to 3 heteroatoms; more preferably from 1 to 6 carbon atoms and 0 to 2 heteroatoms; more preferably from 1 to 4 carbon atoms and 0 to 1 heteroatoms. Where the systems contain heteroatoms, preferably they contain 1 heteroatom. Preferred heteroatoms include O, S, and N; more preferred are O, and N; more preferred is O.

Preferably, $R^2$ is selected from any of the systems defined for $R^1$ above, and H. More preferably, $R^2$ is H.

In some embodiments, either or both of $R^1$ and $R^2$ are unsubstituted. Preferably, $R^1$ is, and $R^2$ is optionally, selected from: (a) a straight or branched $C_1$–$C_4$ alkyl radical; (b) a phenyl ring; (c) a benzyl radical; (d) a heterocyclic radical having a 5- or 6-membered ring; (e) a mono-, poly-, or per-fluoro alkyl systems; said systems comprising from 1 to 4 carbon atoms; (f) a —$(CH_2$—$CH_2$—$O)_p$—OR' radical, wherein p is an integer from 1 to 3, wherein R' is H, or a $C_1$–$C_4$ alkyl radical; and (g) a —$CH_2$—$CH(CH_3))_q$—OR' radical, wherein q is an integer from 1 to 2, wherein R' is H, or a $C_1$–$C_4$ alkyl radical. More preferably, $R^2$ is H, and $R^1$ is selected from: (a) an alkyl radical selected from methyl, ethyl, isopropyl and tert-butyl radicals; (b) a phenyl radical; (c) a benzyl radical; (d) a heterocyclic radical selected from a thiophene ring, a furan ring, a pyrazole ring, a pyrimidine ring, and a pyridine ring; (e) a trifluoromethyl radical; and (f) an alkoxyethyl radical selected from methoxyethyl, ethoxyethyl, and isopropoxyethyl radicals.

Preferred unsubstituted compounds of the invention include compounds A, B, C, and D, below. More preferred are compounds A and B; more preferred is compound A.

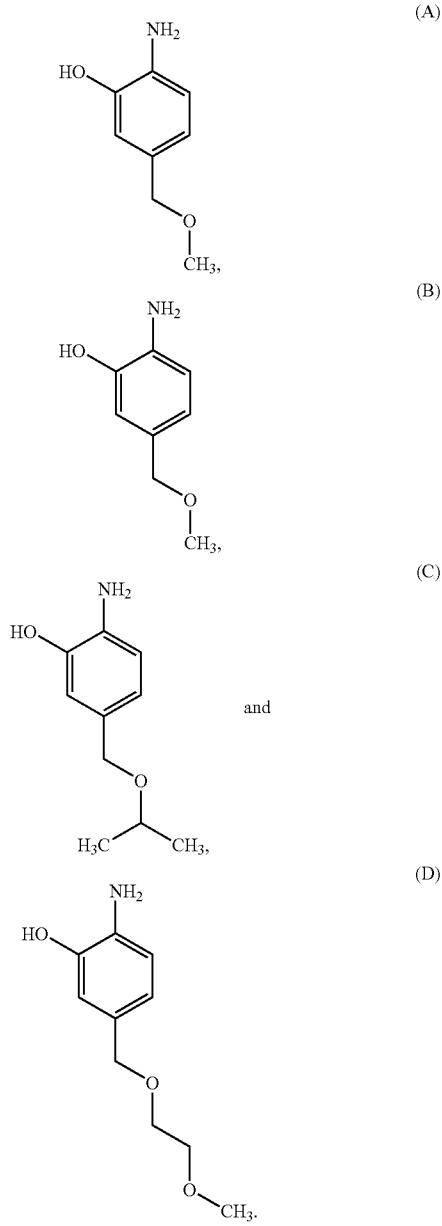

In other embodiments, either or both of $R^1$ and $R^2$ are substituted. Preferably, the substituent(s) is selected from: (a) the group of C-linked monovalent substituents consisting of: (i) substituted or unsubstituted, straight or branched, alkyl, mono- or poly-unsaturated alkyl, heteroalkyl, aliphatic, heteroaliphatic, or heteroolefinic systems, (ii) substituted or unsubstituted, mono- or poly-cyclic aliphatic, aryl, or heterocyclic systems, or (iii) substituted or unsubstituted, mono-, poly-, or per-fluoro alkyl systems; said systems of (i), (ii) and (iii) comprising from 1 to 10 carbon atoms and 0 to 5 heteroatoms selected from O, S, N, P, and Si; (b) the group of S-linked monovalent substituents consisting of $SA^1$, SCN, $SO_2A^1$, $SO_3A^1$, $SSA^1$, $SOA^1$, $SO_2NA^1A^2$, $SNA^1A^2$, and $SONA^1A^2$; (c) the group of O-linked monovalent substituents consisting of $OA^1$, OCN and $ONA^1A^2$; (d) the group of N-linked monovalent substituents consisting of $NA^1A^2$, $(NA^1A^2A^3)^+$, NC, $NA^1OA^2$, $NA^1SA^2$, NCO, NCS, $NO_2$, $N=NA^1$, $N=NOA^1$, $NA^1CN$, $NA^1NA^2A^3$; (e) the group of monovalent substituents consisting of $COOA^1$, $CON_3$, $CONA^1_2$, $CONA^1COA^2$, $C(=NA^1)NA^1A^2$, CHO, CHS, CN, NC, and X; and (f) the group consisting fluoroalkyl monovalent substituents consisting of mono-, poly-, or per-fluoro alkyl systems comprising from 1 to 12 carbon atoms and 0 to 4 heteroatoms.

For the groups (b) to (e), described above, $A^1$, $A^2$, and $A^3$ are monovalent and are independently selected from: (1) H, (2) substituted or unsubstituted, straight or branched, alkyl, mono- or poly-unsaturated alkyl, heteroalkyl, aliphatic, heteroaliphatic, or heteroolefinic systems, (3) substituted or unsubstituted, mono- or poly-cyclic aliphatic, aryl, or heterocyclic systems, or (4) substituted or unsubstituted, mono-, poly-, or per-fluoro alkyl systems; said systems of (2), (3) and (4) comprising from 1 to 10 carbon atoms and 0 to 5 heteroatoms selected from O, S, N, P, and Si; and wherein X is a halogen selected from the group consisting of F, Cl, Br, and I.

Preferred substituents for use herein include those having a Hammett Sigma Para ($\sigma_p$) Value from −0.65 to +0.75, preferably from −0.4 to +0.5. Hammett Sigma Values are described in Advanced Organic Chemistry—Reactions, Mechanisms and Structure (Jerry March, 5$^{th}$ ed. (2001) at pages 368–375). Without being limited by theory, it is believed that substituents having sigma para values in the chosen ranges, when substituted onto $R^1$ and/or $R^2$, may improve the compound's toxicological profile without unduly adding an unfavourable increase in molecular weight that may interfere with the molecule's ability to penetrate the hair shaft. Some preferred substituents and their Hammett Sigma Para values are shown below, in Table 1. Additional substituents and their values are shown in March, at page 370.

TABLE 1

| Substituent | $NH_2$ | OH | H | $COO^-$ | Cl | COOH | $CF_3$ |
|---|---|---|---|---|---|---|---|
| $\sigma_p$ | −0.57 | −0.38 | 0 | 0.11 | 0.24 | 0.44 | 0.53 |

Some preferred substituents for use herein are characterized in that substituting them onto $R^1$ and/or $R^2$ will tend to increase the overall hydrophilicity of the inventive compound versus the same compound, but unsubstitued, i.e. where H takes the place of the substituent, or in the case of multiple substituents, H takes the place of each of them. The use of log P (partition coefficient) is known for measuring the degree to which a chemical entity exhibits hydrophilicity. P is the ratio of the respective concentrations of a compound in a 1:1 solution of octanol and water that has reached equilibrium, at a constant temperature (usually 25 □C) and pressure (usually 760 mmHg). However, P, and hence log P, does not take into consideration variation of pH. Particularly, it does not take into consideration the ionization of compounds at various pH.

Hair coloring compositions are typically formulated at a pH between 9 and 11, preferably at pH 10. Preferably, the inventive compounds are characterized by good hydrophilicity. Accordingly, in one embodiment, substituents that provide good hydrophilicity at pH 10 are preferred for use herein. In order to predict which substituents may provide good hydrophilicity, the inventors have found that log D values are more useful. D is the ratio of the equilibrium concentrations of all species "i" (ionized and non-ionized) of a given molecule "Z", comprising the substituent "Z'", in a 1:1 solution of octanal and water that has reached equilibrium, at a constant temperature (usually 25 □C) and pressure (usually 760 mmHg), and log D may be represented as:

Log $D = \text{Log}(\Sigma[Z_i]_{oct}/\Sigma[Z_i]_{aq})$

If $\Sigma[Z_i]_{oct} > \Sigma[Z_i]_{aq}$, then log D is positive, if $\Sigma[Z_i]_{oct} < \Sigma[Z_i]_{aq}$ then log D is negative, and if $\Sigma[Z_i]_{oct} = \Sigma[Z_i]_{aq}$ then log D=0. Log D values for any compound Z may be calculated using commercially available software packages, e.g. ACD/Labs 6.00, available from Advanced Chemistry Development, Inc. (Canada). Using this software, several log D values at pH 10 were calculated for molecules (Z) comprising preferred substituents (Z') and the same molecules wherein the substituent(s) was replaced with H. These values and the absolute value of the differences between them versus H ("Abs") are shown in Table 2.

ably |log $D_Z$–log $D_H$|>1, wherein log $D_Z$ is log D of the molecule Z with substituent(s) Z', and log $D_H$ is the log D of the molecule Z with hydrogen(s).

In a preferred embodiment, at least one of $R_1$ and $R^2$ is substituted, and the substituent comprises at least one —OH group.

In another preferred embodiment, $R_1$ is, and $R_2$ is optionally, selected from: (a) a phenyl ring substituted by X, a $C_1$–$C_4$ alkyl radical, a $C_{1-C4}$ alkoxy radical, an amino radical, a trifluoromethyl radical, or a $C_1$–$C_4$ alkylamino radical; (b) a benzyl radical substituted by X, a $C_1$–$C_4$ alkyl radical, a $C_1$–$C_4$ alkoxy radical, a nitro radical, an amino radical, a trifluoromethyl radical, or a $C_1$–$C_4$ alkylamino radical; (c) a $C_1$–$C_8$ mono-, di-, or tri-hydroxyalkyl radical; (d) a $C_1$–$C_4$ aminoalkyl radical; (e) a $C_1$–$C_8$ N-alkylaminoalkyl radical; (f) a $C_1$–$C_{12}$ N, N-dialkylaminoalkyl radical; (g) an arylaminoalkyl radical; (h) a $C_1$–$C_8$ alkoxyalkyl

TABLE 2

| Molecule (Z) | H log D | Z' = OH log D | Abs | Z' = NH2 log D | Abs | Z' = COOH log D | Abs |
|---|---|---|---|---|---|---|---|
| 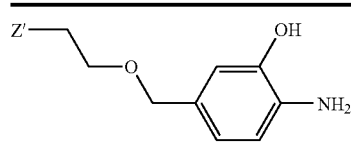 | 0.1 | −1 | 1.1 | −1 | 1.1 | −4.3 | 4.4 |
| 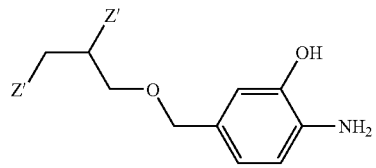 | 0.6 | −1.5 | 2.1 | −2 | 2.6 | −5.2 | 5.8 |
| 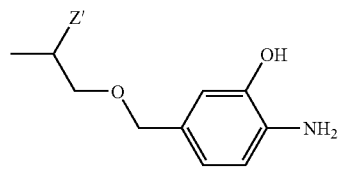 | 0.7 | −0.6 | 1.3 | −0.6 | 1.3 | −3.9 | 4.6 |
| 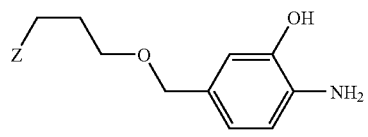 | 0.7 | −0.7 | 1.4 | −0.9 | 1.6 | −4.0 | 4.7 |
| 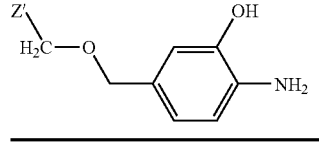 | −0.4 | −1.1 | 0.7 | −1.1 | 0.7 | −4.7 | 4.3 |

In one embodiment, preferred substituents will yield molecules whose log D at pH 10 is negative, i.e. log $D_Z$<0. In another embodiment, preferred subtituents will yield molecules whose log D at pH 10 is such that the absolute value of the difference between the log D of that molecule and the log D of the same molecule with H replacing the substituent is greater than 0.5, preferably greater than 1. As a mathematical relationship: |log $D_Z$–log $D_H$|>0.5, preferably |log $D_Z$–log $D_H$|>1, wherein log $D_Z$ is log D of the radical selected from methoxyalkyl, ethoxyalkyl and phenoxyalkyl; (i) a $C_1$–$C_4$ haloalkyl radical selected from bromoalkyl, chloroalkyl and fluoroalkyl; (j) a $C_1$–$C_4$ carboxyalkyl group; (k) a $C_1$–$C_8$ alkoxycarbonylalkyl radical; (l) a phenyloxycarbonylalkyl radical; (m) a $C_1$–$C_4$ methanesulphonylalkyl radical; (n) a $C_1$–$C_4$ cyanoalkyl radical; (o) an N,N-di(hydroxyalkyl)aminoalkyl radical; and (p) an N-hydroxyalkylaminoalkyl radical.

More preferably, $R^2$ is H, and $R^1$ is selected from: (a) a toluyl radical; (b) a 4-chlorophenyl radical; (c) a 4-methoxyphenyl radical; (d) a 3-methoxyphenyl radical; (e) a 2-methoxyphenyl radical; (f) a hydroxyethyl radical; (g) an aminoethyl radical; (h) a dihydroxyethyl radical; (i) a dihydroxypropyl radical; (j) a hydroxypropyl radical; (k) a hydroxybutyl radical; (l) an N-methylaminomethyl radical; (m) an N,N-dimethylaminomethyl radical; (n) an N-methylaminoethyl radical; (o) an N,N-dimethylaminoethyl radical; (p) an N-ethylaminomethyl radical; (q) an N,N-diethylaminomethyl radical; (r) an N-ethylaminoethyl radical; (s) an N,N-diethylaminoethyl radical; (t) a carboxyethyl radical; (u) a carboxymethyl radical; (v) a methoxycarbonylethyl radical; (w) a methoxycarbonylmethyl radical; (x) an ethoxycarbonylethyl radical; (y) an ethoxycarbonylmethyl radical; (z) a cyanomethyl radical; and (aa) a cyanoethyl radical.

Preferred substituted compounds of the invention include compounds E, F, G, and H, below. More preferred are compounds E and F; more preferred is compound F.

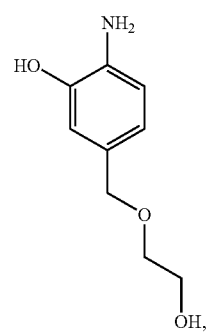
(E)

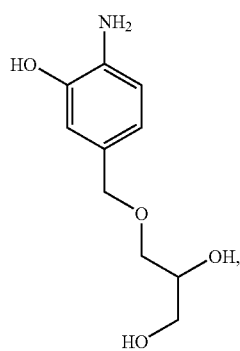
(F)

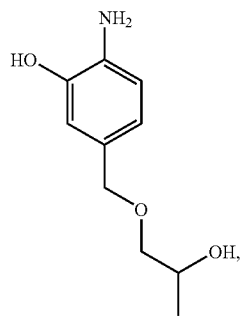
(G)
and

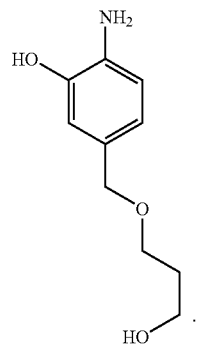
(H)

Compounds according the Formula (I) (above) can be obtained by conventional methods, e.g. by the following general process. By application of the below described reactions, a range of 2-(amino or substituted amino)-5-(substituted oxymethyl)-phenols can be prepared. Such compounds are tri-substituted benzene derivatives, which can be prepared using standard methods of aromatic substitution and functional group manipulation. Typically, any of the three following di-substituted compounds may be used as starting materials (wherein $Y^1$ is hydroxymethyl ($CH_2OH$) or substituted oxymethyl ($CH_2OY^2$, wherein $Y^2$ is defined as $R^1$ above)):

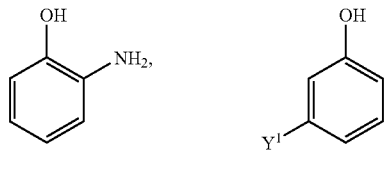

2-aminophenol     3-$Y^1$-phenol

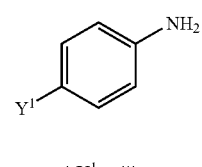

4-$Y^1$-aniline

Consideration of the substitution reactions available and the isomers formed by them shows that the starting material may advantageously be chosen to already comprise the 5-substituent of the final product. Two such commercial starting materials are available with the 5-substituent already present in the 5-substituted 2-nitrophenol which can easily be reduced to the required 2-aminophenol. These are 5-carboxylic acid (1) and 5-carboxaldehyde (4), shown in Reaction Sequence (I):

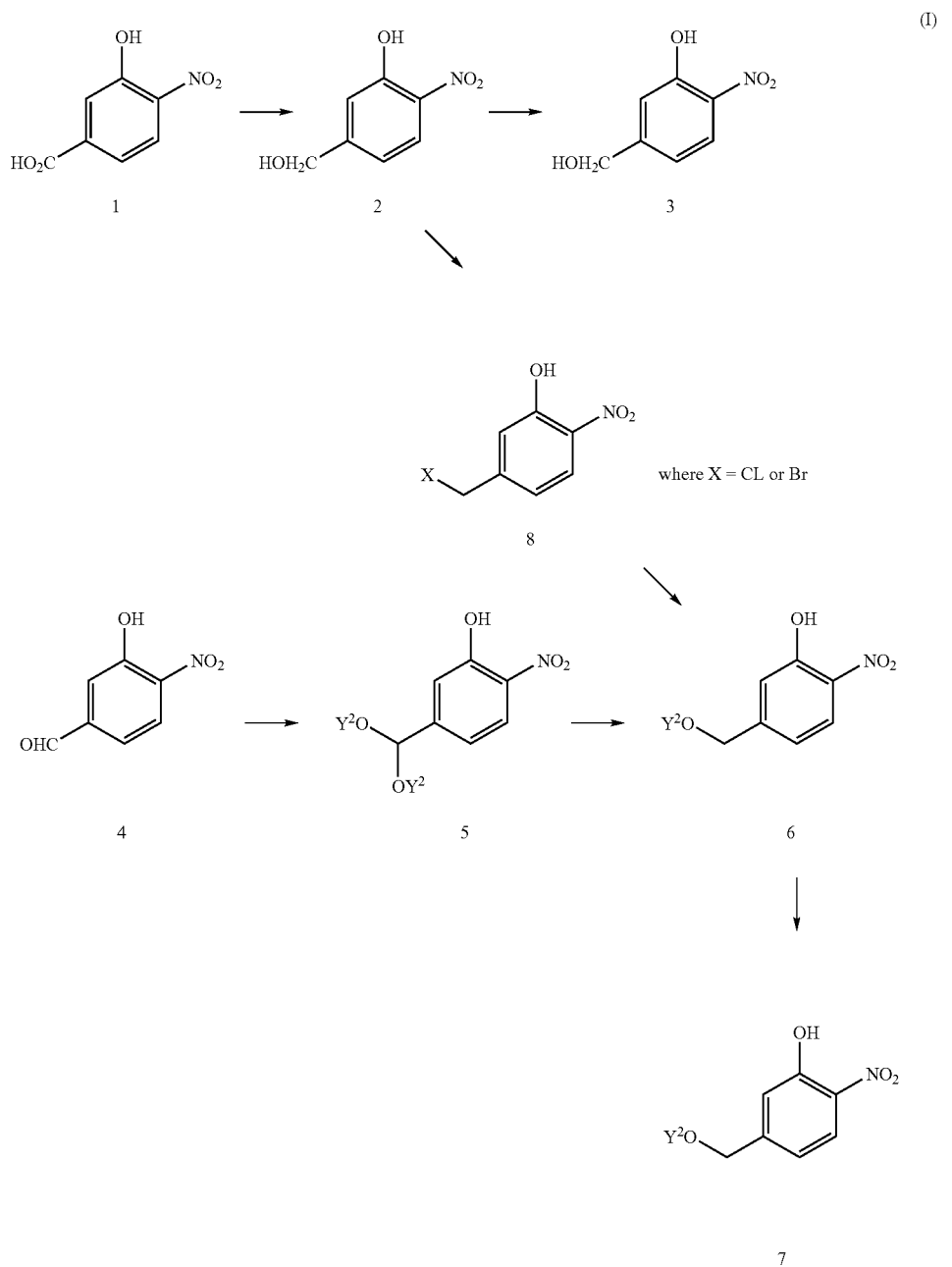

The acid (1) can be reduced to the hydroxymethyl compound (2), followed by reduction of the nitro group to give the desired amine (3) (see Example 2, below). The aldehyde (4) can be converted into the acetal (5), which can be reduced to the substituted oxymethyl compound (6), followed by further reduction of 6 to the amine (7) (see Example 1, below).

The nitro-hydroxymethyl intermediate (2) can also be alkylated at the benzylic alcohol group to give the nitro-ether (6) and hence the amine (7). Furthermore, the same intermediate (2) can be converted into the corresponding chloromethyl or bromomethyl compounds (8) from which the halogen could be displaced by $Y^2O^-$ ions, to give the nitro-ethers (6) and hence the amines (7).

Another readily available di-substituted starting material, 3-hydroxybenzyl alcohol (9), is available. This can be nitrated to give 3-hydroxy-4-nitrobenzylalcohol (2), and hence 4-amino-3-hydroxybenzyl alcohol (3), or it can be substituted on the benzylic oxygen to give 10, and then nitrated to give 6, and reduced to give the amine 7, as shown Reaction Sequence (II):

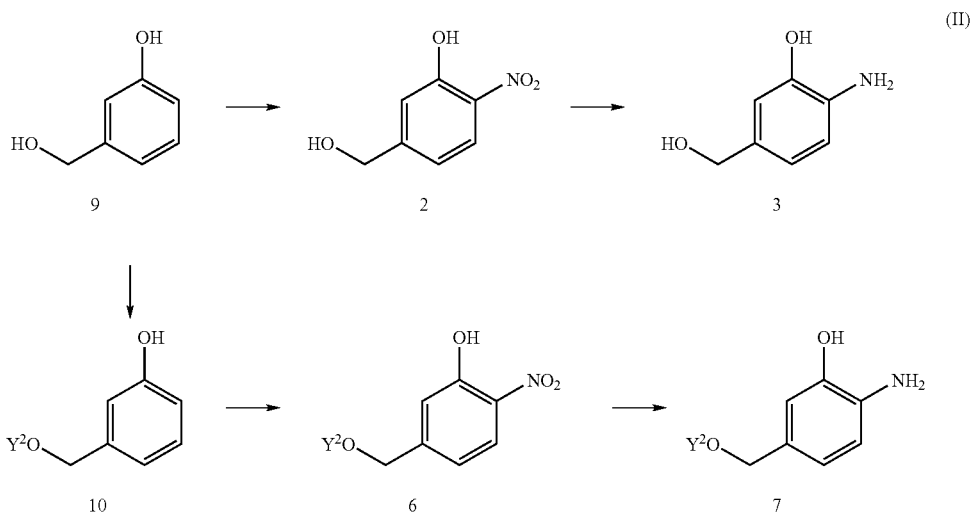

The routes outlined above give amino functionality in the 2-position from reduction of the nitro functionality. In order to achieve molecules according to Formula (I), wherein $R^1$ is something other than H, simple alkylation reactions can be employed to change $NH_2$ to $NHR^1$.

II. Composition Components

The inventive compositions for the oxidative dyeing of keratin fibers comprise a medium suitable for dyeing and a compound of the Formula (II), or its salts with an inorganic or organic acid:

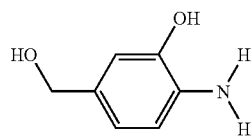

wherein $R^3$ and $R^4$ are monovalent and are independently selected from: (a) substituted or unsubstituted, straight or branched, alkyl, mono- or poly-unsaturated alkyl, heteroalkyl, aliphatic, heteroaliphatic, or heteroolefinic systems, (b) substituted or unsubstituted, mono- or poly-cyclic aliphatic, aryl, or heterocyclic systems, (c) substituted or unsubstituted, mono-, poly-, or per-fluoro alkyl systems; said systems of (a), (b) and (c) comprising from 1 to 12 carbon atoms and 0 to 5 heteroatoms selected from O, S, N, P, and Si, or (d) H. Such compounds will typically be present in an amount ranging from 0.001% to 10%, preferably from 0.01% to 5%, by weight, of the hair dye composition.

For the inventive compositions, preferred $R^3$ ligands will be selected from those ligands defined in the inventive compounds section above, as $R^1$, and will also be selected from H. Preferred $R^4$ ligands will be selected from those ligands defined in the inventive compounds section above, as $R^2$. Preferred compounds for use in the inventive compositions will be selected from those compounds listed in the inventive compounds section above, and will also include 2-amino-5-hydroxymethyl-phenol, shown below:

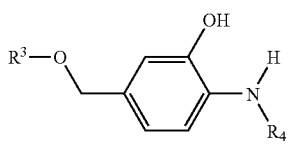

The medium suitable for dyeing may be selected from water, or a mixture of water and at least one organic solvent to dissolve the compounds that would not typically be sufficiently soluble in water. Suitable organic solvents for use herein include, but are not limited to: C1 to C4 lower alkanols (e.g., ethanol, propanol, isopropanol), aromatic alcohols (e.g. benzyl alcohol and phenoxyethanol); polyols and polyol ethers (e.g., carbitols, 2-butoxyethanol, propylene glycol, propylene glycol monomethyl ether, diethylene glycol monoethyl ether, monomethyl ether, hexylene glycol, glycerol, ethoxy glycol), and propylene carbonate. When present, organic solvents are typically present in an amount ranging from 1% to 30%, by weight, of the composition. Preferred solvents are water, ethanol, propanol, isopropanol, glycerol, 1,2-propylene glycol, hexylene glycol, ethoxy diglycol, and mixtures thereof.

The inventive compositions may, in some embodiments, further comprise additional optional components known, conventionally used, or otherwise effective for use in oxidative dye compositions, including but limited to: primary intermediate dye compounds; coupler dye compounds; direct dyes; anionic, cationic, nonionic, amphoteric or zwitterionic surfactants, or mixtures thereof; anionic, cationic, nonionic, amphoteric or zwitterionic polymers, or mixtures thereof; inorganic or organic thickeners; antioxidants and radical scavengers; penetration agents; chelating and sequestering agents; fragrances; buffers; dispersing agents; peroxide stabilizing agents; natural ingredients, e.g. proteins and protein derivatives, and plant materials (e.g. aloe, chamomile and henna extracts); silicones (volatile or non-volatile, modified or non-modified), film-forming agents, ceramides, preserving agents; and opacifiers.

Some adjuvants referred to above, but not specifically described below, which are suitable are listed in the International Cosmetics Ingredient Dictionary and Handbook, (8th ed.; The Cosmetics, Toiletry, and Fragrance Association). Particularly, vol. 2, sections 3 (Chemical Classes) and 4 (Functions) are useful in identifying specific adjuvants to achieve a particular purpose or multipurpose.

Oxidative Dye Compounds

The oxidative dye precursors according to Formula II (above) that are comprised within the inventive compositions may be present alone as dyeing agents, and can advantageously behave both like an oxidation base and like a coupler, e.g. self-coupling compounds. They may also be used in combination with one or more primary intermediates, and/or couplers, and in combination with one or more oxidizing agent. All known coupler and primary intermediate combinations are usable in the inventive compositions. However, in one embodiment, where the compositions contain the oxidative dye precursor 2-amino-5-hydroxymethyl-phenol, they do not contain 2-(amino or substituted amino)-3-amino-phenol oxidative dye precursors. In another embodiment, where the compositions contain the oxidative dye precursor 2-amino-5-hydroxymethyl-phenol, they do not contain 3-amino-phenols having an N atom attached to the benzene ring at the 2-position, the N being part of a ring ligand according to any of the following structures:

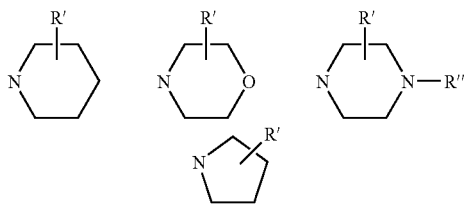

wherein R' is selected from H, —OH, —COOH, aminocarbonyl, or C1 to C4 alkoxy; and R" is selected from H, or C1 to C6 alkyl. In another embodiment, where the compositions contain the oxidative dye precursor 2-amino-5-hydroxymethyl-phenol, they do not contain 3-amino-phenols having an N atom attached to the benzene ring at the 2-position.

The compounds suitable for use in the inventive compositions (including those optionally added), in so far as they are bases, may be used as free bases or in the form of their physiologically compatible salts with organic or inorganic acids, such as hydrochloric, hydrobromic, citric, acetic, lactic, succinic, tartaric, or sulfuric acids, or, in so far as they have aromatic OH groups, in the form of their salts with bases, such as alkali phenolates.

Optional couplers, when present, are typically present in an amount such that in aggregate the concentration of couplers and the compounds of Formula (II) in the composition ranges from 0.002% to 10%, preferably from 0.01% to 5%, by weight, of the composition. Optional primary intermediates, when present, are present in an effective dyeing concentration, typically an amount from 0.001% to 10%, preferably from 0.01% to 5%, by weight, of the composition. The total amount of dye compounds (e.g., optional primary intermediates, optional coupler compounds, and the compounds of Formula (II)) in the hair dyeing compositions of this invention will typically range from 0.002% to 20%, preferably from 0.04% to 10%, more preferably from 0.1% to 7%, by weight, of the hair dyeing composition.

Primary Intermediates

Suitable primary intermediates for use in the compositions described herein include, but are not limited to p-phenylenediamine derivatives, e.g. benzene-1,4-diamine (commonly known as p-phenylenediamine), 2-methyl-benzene-1,4-diamine, 2-chloro-benzene-1,4-diamine, N-phenyl-benzene-1,4-diamine, N-(2-ethoxyethyl)benzene-1,4-diamine, 2-[(4-amino-phenyl)-(2-hydroxy-ethyl)-amino]-ethanol, (commonly known as N,N-bis(2-hydroxyethyl)-p-phenylenediamine) (2,5-diamino-phenyl)-methanol, 1-(2'-Hydroxyethyl)-2,5-diaminobenzene, 2-(2,5-diamino-phenyl)-ethanol, N-(4-aminophenyl)benzene-1,4-diamine, 2,6-dimethyl-benzene-1,4-diamine, 2-isopropyl-benzene-1,4-diamine, 1-[(4-aminophenyl)amino]-propan-2-ol, 2-propyl-benzene-1,4-benzene-1,4-diamine, 1,3-bis[(4-aminophenyl)(2-hydroxyethyl)amino]propan-2-ol, $N^4,N^4$,2-trimethylbenzene-1,4-diamine, 2-methoxy-benzene-1,4-diamine, 1-(2,5-diaminophenyl)ethane-1,2diol, 2,3-dimethyl-benzene-1,4-diamine, N-(4-amino-3-hydroxy-phenyl)-acetamide, 2,6-diethylbenzene-1,4-diamine, 2,5-dimethylbenzene-1,4-diamine, 2-thien-2-ylbenzene-1,4-diamine, 2-thien-3-ylbenzene-1,4-diamine, 2-pyridin-3-ylbenzene-1,4-diamine, 1,1'-biphenyl-2,5-diamine, 2-(methoxymethyl)benzene-1,4-diamine, 2-(aminomethyl) benzene-1,4-diamine, 2-(2,5-diaminophenoxy)ethanol, N-[2-(2,5-diaminophenoxy)ethyl]-acetamide, N,N-dimethylbenzene-1,4-diamine, N,N-diethylbenzene-1,4-diamine, N,N-dipropylbenzene-1,4-diamine, 2-[(4-aminophenyl)(ethyl)amino]ethanol 2-[(4-amino-3-methyl-phenyl)-(2-hydroxy-ethyl)-amino]-ethanol, N-(2-methoxyethyl)-benzene-1,4-diamine, 3-[(4-aminophenyl)amino]propan-1-ol, 3-[(4-aminophenyl)-amino]propane-1,2-diol, N-{4-[(4-aminophenyl)amino]butyl}benzene-1,4-diamine, and 2-[2-(2-{2-[(2,5-diaminophenyl)-oxy]ethoxy}ethoxy)ethoxy]benzene-1,4-diamine; 1,3-Bis(N(2-Hydroxyethyl)-N-(4-amino-phenyl)amino)-2-propanol; 2,2'-[1,2-Ethanediyl-bis-(oxy-2,1-ethanediyloxy)]-bis-benzene-1,4-diamine; N,N-Bis(2-hydroxyethyl)-p-phenylinediamine;

p-aminophenol derivatives such as: 4-amino-phenol (commonly known as p-aminophenol), 4-methylamino-phenol, 4-amino-3-methyl-phenol, 4-amino-2-hydroxymethyl-phenol, 4-amino-2-methyl-phenol, 4-amino-1-hydroxy-2-(2'-hydroxyethylaminomethyl) benzene, 4-amino-2-methoxymethyl-phenol, 5-amino-2-hydroxy-benzoic acid, 1-(5-amino-2-hydroxy-phenyl)-ethane-1,2-diol, 4-amino-2-(2-hydroxy-ethyl)-phenol, 4-amino-3-(hydroxymethyl)phenol, 4-amino-3-fluoro-phenol, 4-amino-2-(aminomethyl)-phenol, 4-amino-2-fluoro-phenol; 1-Hydroxy-2,4-diaminobenzene; 1-(2'-Hydroxyethyloxy)-2,4-diaminobenzene; 2,4-Diamino-5-methylphenetol;

o-phenylenediamine derivatives such as: 3,4-Diaminobenzoic acid and salts thereof;

o-aminophenol derivatives such as: 2-amino-phenol (commonly known as o-aminophenol), 2,4-diaminophenol, 2-amino-5-methyl-phenol, 2-amino-6-methyl-phenol, N-(4-amnino-3-hydroxy-phenyl)-acetamide, and 2-amino-4-methyl-phenol; and heterocyclic derivatives such as: pyrimidine-2,4,5,6-tetramine (commonly known as 2,4,5,6-tetraaminopyridine), 1-methyl-1H-pyrazole-4,5-diamine, 2-(4,5-diamino-1H-pyrazol-1-yl)ethanl, $N^2,N^2$-dimethyl-pyridine-2,5-diamine, 2-[(3-amino-6-methoxypyridin-2-yl)amino]ethanol, 6-methoxy-$N^2$-methyl-pyridine-2,3-diamine, 2,5,6-triaminopyrimidin-4(1H)-one, pyridine-2,5-diamine, 1-isopropyl-1H-pyrazole-4,5-diamine, 1-(4-methylbenzyl)-1H-pyrazole-4,5-diamine, 1-(benzyl)-1H-pyrazole-4,5-diamine, 1-(4-chlorobenzyl)-1H-pyrazole-4,5diamine, pyrazole[1,5-a]-pyrimidine-3,7-diamine, 5,6,7-trimethylpyrazolo[1,5-a]pyrimidin-3-ylamine hydrochloride, 7-methylpyrazolo[1,5-a]pyrimidin-3-ylamine hydrochloride, 2,5,6,7-teramethyl-pyrazolo[1,5-a]pyrimidin-3-ylamine hydrochloride, 5,7-di-tert-butylpyrazolo[1,5-a]pyrimidin-3-ylamine hydrochloride, 5,7-di-trifluoromethyl-pyrazolo[1,5-a]pyrimidin-3-ylamine hydrochloride, 2-methylpyrazolo[1,5-a]pyrimidin-3,7-diamine hydrochloride; 4-Hydroxy-2,5,6-triaminopyrimidine; 1-(2'hydroxyethyl)-amino-3,4-methylene dioxybenzene; and 1-Hydroxyethyl-4,5-diaminopyrazole sulphate.

Preferred primary intermediates include but are not limited to: p-phenylenediamine derivatives such as: 2-methyl-benzene-1,4-diamine; benzene-1,4-diamine; 1-(2,5-diamino-phenyl)-ethanol; 2-(2,5-diamino-phenyl)-ethanol; N-(2-methoxyethyl)benzene-1,4-diamine; 2-[(4-amino-phenyl)-(2-hydroxy-ethyl)-amino]-ethanol; 1-(2,5-diaminophenyl)ethane-1,2-diol; 1-(2'-Hydroxyethyl)-2,5-diaminobenzene; 1,3-Bis(N(2-Hydroxyethyl)-N-(4-amino-phenyl)amino)-2-propanol; 2,2'-[1,2-Ethanediyl-bis-(oxy-2,1-ethanediyloxy)]-bis-benzene-1,4-diamine; N,N-Bis(2-hydroxyethyl)-p-phenylinediamine; and mixtures thereof;

p-aminophenol derivatives such as: 4-amino-phenol, 4-methylamino-phenol, 4-amino-3-methyl-phenol, 4-amino-2-methoxymethyl-phenol; 1-(5-amino-2-hydroxyphenyl)-ethane-1,2-diol; 1-Hydroxy-2,4-diaminobenzene; 1-(2'-Hydroxyethyloxy)-2,4-diaminobenzene; 4-Amino-2-aminomethylphenol; 2,4-Diamino-5-methylphenetol; 4-Amino-1-hydroxy-2-(2'-hydroxyethylaminomethyl)benzene; 1-methoxy-2-amino-4-(2'hydroxyethylamino)benzene; 5-aminosalicylic acid and salts thereof; and mixtures thereof;

o-phenylenediamine derivatives such as: 3,4-Diaminobenzoic acid and salts thereof;

o-aminophenol derivatives such as: 2-amino-phenol, 2-amino-5-methyl-phenol, 2-amino-6-methyl-phenol, N-(4-amino-3-hydroxy-phenyl)-acetamide; 2-amino-4-methyl-phenol; and mixtures thereof; and heterocyclic derivatives such as: pyrimidine-2,4,5,6-tetramine; 1-methyl-1H-pyrazole-4,5-diamine; 2-(4,5-diamino-1H-pyrazol-1-yl)ethanol; 1-(4-methylbenzyl)-1H-pyrazole-4,5-diamine; 1-(benzyl)-1H-pyrazole-4,5-diamine; $N^2,N^2$-dimethyl-pyridine-2,5-diamine; 4-Hydroxy-2,5,6-triaminopyrimidine; 1-(2'hydroxyethyl)-amino-3,4-methylene dioxybenzene; and 1-Hydroxyethyl-4,5-diaminopyrazole sulphate; and mixtures thereof.

More preferred primary intermediates include: 2-methyl-benzene-1,4-diamine; benzene-1,4-diamine; N,N-Bis(2-hydroxyethyl)-p-phenylinediamine; 4-amino-phenol; 4-methylamino-phenol; 4-amino-3-methyl-phenol; 1-Hydroxy-2,4-diaminobenzene; 2-amino-phenol; 2-amino-5-methyl-phenol; 2-amino-6-methyl-phenol; 1-methyl-1H-pyrazole-4,5-diamine; 1-Hydroxyethyl-4,5-diaminopyrazole sulphate; 2-(4,5-diamino-1H-pyrazol-1-yl)ethanol; and mixtures thereof.

Couplers

Suitable couplers for use in the compositions described herein include, but are not limited to: phenols, resorcinol and naphthol derivatives such as: naphthalene-1,7-diol, benzene-1,3-diol, 4-chlorobenzene-1,3-diol, naphthalen-1-ol, 2-methyl-naphthalen-1-ol, naphthalene-1,5-diol, naphthalene-2,7-diol, benzene-1,4-diol, 2-methyl-benzene-1,3-diol, 7-amino-4-hydroxy-naphthalene-2-sulfonic acid, 2-isopropyl-5-methylphenol, 1,2,3,4-tetrahydro-naphthalene-1,5-diol, 2-chloro-benzene-1,3-diol, 4-hydroxy-naphthalene-1-sulfonic acid, benzene-1,2,3-triol, naphthalene-2,3-diol, 5-dichloro-2-methylbenzene-1,3-diol, 4,6-dichlorobenzene-1,3-diol, 2,3-dihydroxy-[1,4]naphthoquinone; and 1-Acetoxy-2-methylnaphthalene;

m-phenylenediamines such as: 2,4-diaminophenol, benzene-1,3-diamine, 2-(2,4-diamino-phenoxy)-ethanol, 2-[(3-amino-phenyl)-(2-hydroxy-ethyl)-amino]-ethanol, 2-mehyl-benzene-1,3-diamine, 2-[[2-(2,4-diamino-phenoxy)-ethyl]-(2-hydroxy-ethyl)-amino]-ethanol, 4-{3-[(2,4-diaminophenyl)oxy]propoxy}benzene-1,3-diamine, 2-(2,4-diamino-phenyl)-ethanol, 2-(3-amino-4-methoxy-phenylamino)-ethanol, 4-(2-amino-ethoxy)-benzene-1,3-diamine, (2,4-diamino-phenoxy)-acetic acid, 2-[2,4-diamino-5-(2-hydroxy-ethoxy)-phenoxy]-ethanol, 4-ethoxy-6-methyl-benzene-1,3-diamine, 2-(2,4-diamino-5-methyl-phenoxy)-ethanol, 4,6-dimethoxy-benzene-1,3-diamine, 2-[3-(2-hydroxy-ethylamino)-2-methyl-phenylamino]-ethanol, 3-(2,4-diamino-phenoxy)-propan-1-ol, N-[3-(dimethylamino)phenyl]urea, 4-methoxy-6-methyl-benzene-1,3-diamine, 4-fluoro-6-methylbenzene-1,3-diamine, 2-({3-[(2-hydroxyethyl)amino]4,6-dimethoxyphenyl}-amino)ethanol, 3-(2,4-diaminophenoxy)-propane-1,2-diol, 2-[2-amino-4-(methylamino)-phenoxy]ethanol, 2-[(5-amino-2-ethoxy-phenyl)-(2-hydroxy-ethyl)-amino]-ethanol, 2-[(3-aminophenyl)amino]ethanol, 2,4-Diamino-5-(2'-hydroxyethyloxy)toluene; N,N-Dimethyl-3-ureidoaniline; N-(2-aminoethyl)benzene-1,3-diamine, 4-{[(2,4-diaminophenyl)oxy]methoxy}-benzene-1,3-diamine, 1-methyl-2,6-bis(2-hydroxyethylamino)benzene; and 2,4-dimethoxybenzene-1,3-diamine;

m-aminophenols such as: 3-amino-phenol, 2-(3-hydroxy-4-methyl-phenylamino)-acetamide, 2-(3-hydroxy-phenylamino)-acetamide, 5-amino-2-methyl-phenol, 5-(2-hydroxy-ethylamino)-2-methyl-phenol, 5-amino-2,4-dichloro-phenol, 3-amino-2-methyl-phenol, 3-amino-2chloro-6-methyl-phenol, 5-amino-2-(2-hydroxy-ethoxy)-phenol, 2-chloro-5-(2,2,2-trifluoro-ethylamino)-phenol, 5-amino-4-chloro-2-methyl-phenol, 3-cyclopentylamino-phenol, 5-[(2-hydroxyethyl)amino]4-methoxy-2-methylphenol, 5-amino-4-methoxy-2-methylphenol, 3-(dimethylamino)phenol, 3-(diethylamino)phenol, 5-amino-4-fluoro-2-methylphenol, 5-amino-4-ethoxy-2-methylphenol, 3-amino-2,4-dichloro-phenol, 3-[(2-methoxyethyl)amino]phenol, 3-[(2-hydroxyethyl)amino]phenol, 5-amino-2-ethyl-phenol, 5-amino-2-methoxyphenyl, 5-[(3-hydroxy-propyl)amino]-2-methylphenol, 3-[(3-hydroxy-2-methylphenyl)-amino]propane-1,2-diol, 3-[(2-hydroxyethyl)amino]-2-methylphenol; 1-Methyl-2-hydroxy-4-(2'-hydroxyethyl)amino-benzene; 1,3-Bis-(2,4-Diaminophenoxy)propane; 1-Hydroxy-2-methyl-5-amino-6-chlorobenzene; and heterocyclic derivatives such as: 3,4-dihydro-2H-1,4-benzoxazin-6-ol, 4-methyl-2-phenyl-2,4-dihydro-3H-pyrazol-3-one, 6-methoxyquinolin-8-amine, 4-methylpyridine-2,6-diol, 2,3-dihydro-1,4-benzodioxin-5-ol, 1,3-benzodioxol-5-ol, 2-(1,3-benzodioxol-5-ylamino)ethanol, 3,4-dimethylpyridine-2,6-diol, 5-chloropyridine-2,3-diol, 2,6-dimethoxypyridine-3,5-diamine, 1,3-benzodioxol-5-amine, 2-{[3,5-diamino-6-(2-hydroxy-ethoxy)-pyridin-2-yl]oxy}-ethanol, 1H-indol 4-ol, 5-amino-2,6-dimethoxypyridin-3-ol, 1H-indole-5,6-diol, 1H-indol-7-ol, 1H-indol-5-ol, H-indol-6-ol, 6-bromo-1,3-benzodioxol-5-ol, 2-aminopyridin-3-ol, pyridine-2,6-diamine, 3-[(3,5diaminopyridin-2yl)oxy]propane-1,2-diol, 5-[(3,5-diaminopyridin-2-yl)oxy]pentane-1,3-diol, 1H-indole-2,3-dione, indoline-5,6-diol, 3,5-dimethoxypyridine-2,6-diamine, 6-methoxypyridine-2,3-diamine; 3,4-dihydro-2H-1,4-benzoxazin-6-amine; 4-hydroxy-N-methylindole, 1H-5-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole, 6-methylpyrazolo-[1,5-a]benzimidazole, 2,6-dihydroxypyridine, 2,6-dihydroxy-3,4-dimethylpyridine, 5-methylpyrazolo[5,1-e]-1,2,3-triazole, 5-methyl-6-chloropyrazolo[5,1-e]-1,2,3,-triazole, 5-phenylpyrazolo[5,1-e]-1,2,3-triazole and addition salts, 1H-2,6-dimethylpyrazolo[1,5-b]-1,2,4-triazole tosylate, 7,8-dicyano-4-methylimidazolo-[3,2-a]imidazole, 2,7-dimethylpyrazolo[1,5-a]pyrimidin-5-one, 2,5-dimethylpyrazolo[1,5-a]pyrimidin-7-one, and 2-methyl-5-methoxymethyl-pyrazolo[1,5-a]pyrimidin-7-one; 6-Hydroxybenzomorpholine; and 3-Amino-2-methylamino-6-methoxypyridine; 1-Phenyl-3-methyl-5-pyrazolone-2,4-dihydro-5,2-phenyl-3H-pyrazole-3-one.

Preferred couplers include but are not limited to: phenol, resorcinol, and naphthol derivatives such as: naphthalene-1,7-diol, benzene-1,3-diol, 4-chlorobenzene-1,3-diol, naphthalen-1-ol, 2-methyl-naphthalen-1-ol, naphthalene-1,5-diol, naphthalene-2,7-diol, benzene-1,4-diol, 2-methyl-benzene-1,3-diol, and 2-isopropyl-5-methylphenol; 1,2,4-Trihydroxybenzene; 1-Acetoxy-2-methylnaphthalene; and mixtures thereof;

m-phenylenediamine derivatives such as: benzene-1,3-diamine, 2-(2,4-diamino-phenoxy)-ethanol, 4-{3-[(2,4-diaminophenyl)oxy]propoxy }benzene-1,3-diamine, 2-(3-amino-4-methoxy-phenylamino)-ethanol, 2-[2,4-diamino-5-(2-hydroxy-ethoxy)-phenoxy]-ethanol, and 3-(2,4-diamino-phenoxy)-propan-1-ol; 2,4-Diamino-5-(2'-hydroxyethyloxy)toluene; N,N-Dimethyl-3-ureidoaniline; 2,4-Diamino-5-fluorotoluenesulfatehydrate; 1-methyl-2,6-bis(2-hydroxyethylamino)benzene; and mixtures thereof;

m-aminophenol derivatives such as: 3-amino-phenol, 5-amino-2-methyl-phenol, 5-(2-hydroxy-ethylamino)-2-methyl-phenol, and 3-amino-2-methyl-phenol; 1-Methyl-2-hydroxy-4-(2'-hydroxyethyl)aminobenzene; 1-Hydroxy-3-amino-2,4-dichlorobenzene; 1,3-Bis-(2,4-Diaminophenoxy)propane; 1-Hydroxy-2-methyl-5-amino-6-chlorobenzene; 5-Amino-4-chloro-2-methylphenol; and mixtures thereof; and heterocyclic derivatives such as: 3,4-dihydro-2H-1,4-benzoxazin-6-ol, 4-methyl-2-phenyl-2,4-dihydro-3H-pyrazol-3-one, 1,3-benzodioxol-5-ol, 1,3-benzodioxol-5-amine, 1H-indol-4-ol, 1H-indole-5,6-diol, 1H-indol-7-ol, 1H-indol-5-ol, 1H-indol-6-ol, 1H-indole-2,3-dione, pyridine-2,6-diamine, 2-aminopyridin-3-ol, 4-hydroxy-N-methylindole, 1H-5-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole, 6-methylpyrazolo-[1,5-a]benzimidazole; 2,6-dihydroxypyridine; 2,6-dihydroxy-3,4-dimethylpyridine; 6-Hydroxybenzomorpholine; 2,6-Dihydroxy-3,4-dimethylpyridine; 3,5-Diamino-2,6-dimethoxypyridine; 3-Amino-2-methylamino-6-methoxypyridine; 1-Phenyl-3-methyl-5-pyrazolone-2,4-dihydro-5,2-phenyl-3H-pyrazole-3-one; and mixtures thereof.

More preferred couplers include: benzene-1,3-diol; 4-chlorobenzene-1,3-diol; 2-methyl-benzene-1,3-diol; benzene-1,3-diamine; 3-amino-phenol; 5-amino-2-methyl-phenol; 1-Methyl-2-hydroxy-4-(2'-hydroxyethyl)aminobenzene; 4-methyl-2-phenyl-2,4-dihydro-3H-pyrazol-3-one; 2-aminopyridin-3-ol; 1-phenyl-3-methylpyrazol-5-one; 1-Phenyl-3-methyl-5-pyrazolone-2,4-dihydro-5,2-phenyl-3H-pyrazole-3-one; and mixtures thereof.

Primary Intermediate-Coupler Combinations

Preferred primary intermediate and coupler combinations include, but are not limited to: (a) resorcinol, 4-amino-m-cresol, 2-methylresorcinol, 4-amino-2-hydroxytoluene, m-aminophenol and 2-amino-4-hydroxyethyl anisole sulphate; (b) resorcinol, 4-Amino-m-cresol, 2-methyl-resorcinol, 4-amino-2-hydroxytoluene, m-aminophenol, 2-amino-4-hydroxyethyl anisole sulphate, 1-napthol and toluene-2,5-diamine; (c) 2-methyl-5-hydroxyethylaminophenol, resorcinol, toluene-2,5-diamine, m-aminophenol, p-aminophenol and p-methylaminophenol; (d) 2-methyl-5-hydroxyethylaminophenol, m-aminophenol, p-aminophenol, p-methylaminophenol and p-phenylenediamine; (e) 1-hydroxyethyl-4,5-diamino pyrazole sulphate and m-aminophenol; and (f) 2-methylresorcinol, p-aminophenol, 4-amino-2-hydroxytoluene, p-phenylenediamine and N,N-Bis(2-hydroxyethyl)-p-phenylenediamine.

Direct Dyes

The inventive compositions may also comprise compatible direct dyes, in an amount sufficient to provide additional coloring, particularly with regard to intensity. Typically, such an amount will range from 0.05% to 4%, by weight, of the composition. Suitable direct dyes include but are not limited to: Acid Yellow 1, Acid Orange 3, Disperse Red 17, Basic Brown 17, Acid Black 52, Acid Black 1, Disperse Violet 4, 4-Nitro-o-Phenylenediamine, 2-Nitro-p-Phenylenediamine, Picramic Acid, HC Red No. 13, 1,4-Bis-(2'-Hydroxyethyl)-amino-2-nitrobenzene, HC Yellow No. 5, HC Red No. 7, HC Blue No. 2, HC Yellow No. 4, HC Yellow No. 2, HC Orange No. 1, HC Red No. 1, 2-Chloro-5-nitro-N-Hydroxyethyl-p-phenylenediamine, HC Red No. 3, 4-Amino-3-nitrophenol, 2-Hydroxyethylamino-5-nitroanisole, 3-nitro-p-Hydroxyethylaminophenol, 2-amino-3-nitrophenol, 6-nitro-o-toluidine, 3-methylamino-4-nitrophenoxyethanol, 2-nitro-5-glycerymethylanaline, HC Yellow No. 11, HC Violet No. 1, HC Orange No. 2, HC Orange No. 3, HC Yellow No. 9, 4-Nitrophenyl Aminoethylurea, HC Red No. 10, HC Red No. 11, 2-Hydroxyethyl picramic acid, HC Blue No. 12, HC Yellow No. 6, Hydroxyethyl-2-nitro-p-toluidine, HC Yellow No. 12, HC Blue No. 10, HC Yellow No. 7, HC Yellow No. 10, HC Blue No. 9, N-ethyl-3-nitro PABA, 4-amino-2-nitrophenyl-amine-2'-carboxylic acid, 2-chloro-6-ethylamino-4-nitrophenol, 6-Nitro-2,5-pyridinediamine, HC Violet No. 2, 2-amino-6-chloro-4-nitrophenol, 4-hydroxypropylamino-3-nitrophenol, HC Yellow No. 13, 1,2,3,4-Tetrahydro-6-nitrochinoxalin, HC Red No. 14, HC Yellow No. 15, HC Yellow No. 14, 3-Amino-6-methylamino-2-nitropyridine, 2,6-diamino-3-((pyridine-3-yl)azo)pyridine, Basic Red No. 118, Basic Orange No. 69, N-(2-nitro-4-aminophenyl)-allylamine, 4-[(4-Amino-3-methylphenyl)(4-Imino-3-methyl-2,5-Cyclohexadien-1-ylidene) Methyl]-2-Methyl-benzeneamine-Hydrochloride, 1H-Imidazolium,2-[[4-(dimethyl-amino)phenyl]azo]-1,3-dimethylchloride, Pyridinium, 1-methyl-4-[(methylphenyl-hydrazono)methyl]-, methyl sulfate, 1H-Imidazolium, 2-[(4-aminophenyl)azo]-1,3-dimethyl, chloride, Basic Red 22, Basic Red 76, Basic Brown 16, Basic Yellow 57, 7-(2',4'-Dimethyl-5'-sulfophenylazo)-5-sulfo-8-hydroxynaphthalene, Acid Orange 7, Acid Red 33, 1-(3'-Nitro-5'-sulfo-6'-oxophenylazo)-oxo-naphthalene chromium complex, Acid Yellow 23, Acid Blue 9, Basic Violet 14, Basic Blue 7, Basic Blue 26, Sodium salt of mixture of mono- & disulfonic acids (mainly the latter) of quinophthlanone or 2-quinolylindandione, Basic Red 2, Basic Blue 99, Disperse Red 15, Acid Violet 43, Disperse Violet 1, Acid Blue 62, Pigment Blue 15, Acid Black 132, Basic Yellow 29, Disperse Black 9, 1-(N-Methylmorpholinium-propylamino)-4-hydroxy-anthraquinone methylsulfate, HC Blue No. 8, HC Red No. 8, HC Green No. 1, HC Red No. 9, 2-Hydroxy-1,4-naphthoquinone, Acid Blue 199, Acid Blue 25, Acid Red 4, Henna Red, Indigo, Cochenille, HC Blue 14, Disperse Blue 23, Disperse Blue 3, Violet 2, Disperse Blue 377, Basic Red 51, Basic Orange 31, Basic Yellow 87, and mixtures thereof. Preferred direct dyes include but are not limited to: Disperse Black 9, HC Yellow 2, HC Yellow 4, HC Yellow 15, 4-nitro-o-phenylenediamine, 2-amino-6-chloro-4-nitrophenol, HC Red 3, Disperse Violet 1, HC Blue 2, Disperse Blue 3, Disperse Blue 377, Basic Red 51, Basic Orange 31, Basic Yellow 87, and mixtures thereof.

Oxidizing Agent

The developer compositions suitable for use with the inventive compositions may comprise an oxidizing agent, present in an amount sufficient to bleach melanin pigment in hair and/or cause formation of dye chromophores from oxidative dye precursors (including primary intermediates and/or couplers when present). Typically, such an amount ranges from 1% to 20%, preferably from 3% to 15%, more preferably from 6% to 12%, by weight, of the developer composition. Inorganic peroxygen materials capable of yielding hydrogen peroxide in an aqueous medium are preferred, and include but are not limited to: hydrogen peroxide; inorganic alkali metal peroxides (e.g. sodium periodate and sodium peroxide); organic peroxides (e.g. urea peroxide, melamine peroxide); inorganic perhydrate salt bleaching compounds (e.g. alkali metal salts of perborates, percarbonates, perphosphates, persilicates, and persulphates, preferably sodium salts thereof), which may be incorporated as monohydrates, tetrahydrates, etc.; alkali metal bromates; enzymes; and mixtures thereof. Preferred is hydrogen peroxide.

Thickeners

The inventive compositions may comprise a thickener in an amount sufficient to provide the composition with a viscosity so that it can be readily applied to the hair without unduly dripping off the hair and causing mess. Typically, such an amount will be at least 0.1%, preferably at least 0.5%, more preferably, at least 1%, by weight, of the composition.

Preferred for use herein are salt tolerant thickeners, including but not limited to: xanthan, guar, hydroxypropyl guar, scleroglucan, methyl cellulose, ethyl cellulose (available as AQUACOTE™), hydroxyethyl cellulose (NATROSOL™), carboxymethyl cellulose, hydroxypropylmethyl cellulose, microcrystalline cellulose, hydroxybutylmethyl cellulose, hydroxypropyl cellulose (available as KLUCEL™), hydroxyethyl ethyl cellulose, cetyl hydroxyethyl cellulose (available as NATROSOL™ Plus 330), N-vinylpyrollidone (available as POVIDONE™), Acrylates/Ceteth-20 Itaconate Copolymer (available as STRUCTURE™ 3001), hydroxypropyl starch phosphate (available as STRUCTURE™ ZEA), polyethoxylated urethanes or polycarbamyl polyglycol ester (e.g. PEG-150/Decyl/SMDI copolymer (available as ACULYN™ 44), PEG-150/Stearyl/SMDI copolymer available as ACULYN™ 46), trihydroxystearin (available as THIXCIN™), acrylates copolymer (e.g. available as ACULYN™ 33) or hydrophobically modified acrylate copolymers (e.g. Acrylates/Steareth-20 Methacrylate Copolymer (available as ACULYN™ 22), non-ionic amphophilic polymers comprising at least one fatty chain and at least one hydrophilic unit selected from polyether urethanes comprising at least one fatty chain, and blends of Ceteth—10 phosphate, Di-cetyl phosphate and Cetearyl alcohol (available as CRODAFOS™ CES).

Chelants

The inventive compositions may comprise chelants in an amount sufficient to reduce the amount of metals available to interact with formulation components, particularly oxidizing agents, more particularly peroxides. Typically such an amount will range from at least 0.25%, preferably at least 0.5%, by weight, of the composition. Suitable chelants for use herein include but are not limited to: diamine-N,N'-dipolyacid, monoamine monoamide-N,N'-dipolyacid, and N,N'-bis(2-hydroxybenzyl)ethylenediamine-N,N'-diacetic acid chelants (preferably EDDS (ethylenediaminedisuccinic acid)), carboxylic acids (preferably aminocarboxylic acids), phosphonic acids (preferably aminophosphonic acids) and polyphosphoric acids (in particular straight polyphosphoric acids), their salts and derivatives.

pH Modifiers and Buffering Agents

The inventive compositions may further comprise a pH modifier and/or buffering agent in an amount that is sufficiently effective to adjust the pH of the composition to fall within a range from 3 to 13, preferably from 8 to 12, more preferably from 9 to 11. Suitable pH modifiers and/or buffering agents for use herein include, but are not limited to: ammonia, alkanolamides such as monoethanolamine, diethanolamine, triethanolamine, monopropanolamine, dipropanolamine, tripropanolamine, tripropanolamine, 2-amino-2-methyl-1-propanol, and 2-amino-2-hydroxymethyl-1,3,-propandiol and guanidium salts, alkali metal and ammonium hydroxides and carbonates, preferably sodium hydroxide and ammonium carbonate, and acidulents such as inorganic and inorganic acids, e.g., phosphoric acid, acetic acid, ascorbic acid, citric acid or tartaric acid, hydrochloric acid, and mixtures thereof.

Carbonate Ion Source and Radical Scavenger System

The inventive compositions may comprise a system comprising a source of carbonate ions, carbamate ions and or hydrocarbonate ions, and a radical scavenger, in a sufficient amount to reduce damage to the hair during the coloring process. Typically, such an amount will range from 0.1% to 15%, preferably 0.1% to 10%, more preferably 1% to 7%, by weight of the composition, of the carbonate ion, and from 0.1% to 10%, preferably from 1% to 7%, by weight of the composition, of radical scavenger. Preferably, the radical scavenger is present at an amount such that the ratio of radical scavenger to carbonate ion is from 1:1 to 1:4. The radical scavenger is preferably selected such that it is not an identical species as the alkalizing agent.

Suitable sources for the ions include but are not limited to: sodium carbonate, sodium hydrogen carbonate, potassium carbonate, potassium hydrogen carbonate, guanidine carbonate, guanidine hydrogen carbonate, lithium carbonate, calcium carbonate, magnesium carbonate, barium carbonate, ammonium carbonate, ammonium hydrogen carbonate and mixtures thereof. Preferred sources of carbonate ions are sodium hydrogen carbonate and potassium hydrogen carbonate. Also preferred are ammonium carbonate, and ammonium hydrogen carbonate.

The radical scavenger is a species that can react with a carbonate radical to convert the carbonate radical by a series of fast reactions to a less reactive species. Preferably, when the radical scavenger comprises an N atom, it has a pKa>7 to prevent the protonation of the nitrogen. Preferred radical scavengers may be selected from the classes of alkanolamines, amino sugars, amino acids and mixtures thereof, and may include, but are not limited to: monoethanolamine, 3-amino-1-propanol, 4-amino-1-butanol,5-amino-1-pentanol, 1-amino-2-propanol, 1-amino-2-butanol, 1-amino-2- pentanol, 1-amino-3-pentanol, 1-amino-4-pentanol, 3-amino-2-methylpropan-1-ol, 1-amino-2-methylpropan-2-ol, 3-aminopropane-1,2-diol, glucosamine, N-acetylglucosamine, glycine, arginine, lysine, proline, glutamine, histidine, serine, tryptophan and potassium, sodium and ammonium salts of the above and mixtures thereof. Other preferred radical scavenger compounds include benzylamine, glutamic acid, imidazole, di-tert-butylhydroxytoluene, hydroquinone, catechol and mixtures thereof.

III. Methods of Manufacture

The compounds of this invention may be obtained using conventional methods. A general description of how to make the compounds is provided above and specific examples are provided below. The compositions of this invention may also be obtained using conventional methods. The hair dyeing compositions may be formed as solutions, preferably as aqueous or aqueous-alcohol solutions. The hair dye product compositions may preferably be formed as thick liquids, creams, gels, or emulsions whose composition is a mixture of the dye compound and other dye ingredients with conventional cosmetic additive ingredients suitable for the particular preparation.

IV. Methods of Use

The inventive hair dyeing compositions may be used by admixing them with a suitable oxidant, which reacts with the oxidative dye precursors to develop the hair dye product composition. The oxidant is usually provided in an aqueous composition, i.e. developer composition, which normally is provided as a separate component of the finished hair dyeing product system and present in a separate container. The developer composition may also contain, to the extent compatible, various ingredients needed to form the developer composition, e.g. peroxide stabilizers, foam formers, etc., and may incorporate one or more of the adjuvants referred to above. Upon mixing the hair dyeing composition and the developer composition to form a hair dye product composition, the adjuvants are provided in the hair dye product composition as it is applied to the hair to achieve desired product attributes, e.g., pH, viscosity, rheology, etc.

The hair dyeing product composition as it is applied to the hair, can be weakly acidic, neutral or alkaline according to their composition, typically having a pH from 6 to 11, preferably from 7 to 10, more preferably from 8 to 10. The pH of the developer composition is typically acidic, and generally the pH is from 2.5 to 6.5, preferably from 3 to 5. The pH of the hair dye and developer compositions may be adjusted using a pH modifier as mentioned above.

In order to use the hair dyeing product composition, the above-described compositions are mixed immediately prior to use and a sufficient amount of the mixture is applied to the hair, according to the hair abundance, generally from 60 to 200 grams. Upon such preparation the hair dye product composition is applied to the hair to be dyed and remains in contact with the hair for an amount of time effective to dye the hair. Typically, the hair dye product composition is allowed to act on the hair for 2 to 60, preferably 15 to 45, more preferably, 30 minutes, at a temperature ranging from 15□ to 50° C. Thereafter, the hair is rinsed with water, to remove the hair dye product composition and dried. If necessary, the hair is washed with a shampoo and rinsed, e.g., with water or a weakly acidic solution, such as a citric acid or tartaric acid solution, and dried. Optionally, a separate conditioning product may also be provided.

Together, the hair dyeing composition and the developer composition form a system for dyeing hair. This system may be provided as a kit comprising in a single package separate containers of the hair dyeing composition, the developer composition, the optional conditioner or other hair treatment product, and instructions for use

EXAMPLES

The following are non-limiting examples of embodiments of this invention. In the examples, all concentrations are listed as weight percent, unless otherwise specified. As is apparent to the skilled person, the selection of ingredients will vary depending on the physical and chemical characteristics of the particular ingredients chosen to make this invention.

Example 1

Synthesis of 2-amino-5-methoxymethyl-phenol

This example shows how to make a preferred compound of the invention, which is suitable for use in the compositions of the invention, according to Reaction Sequence (III):

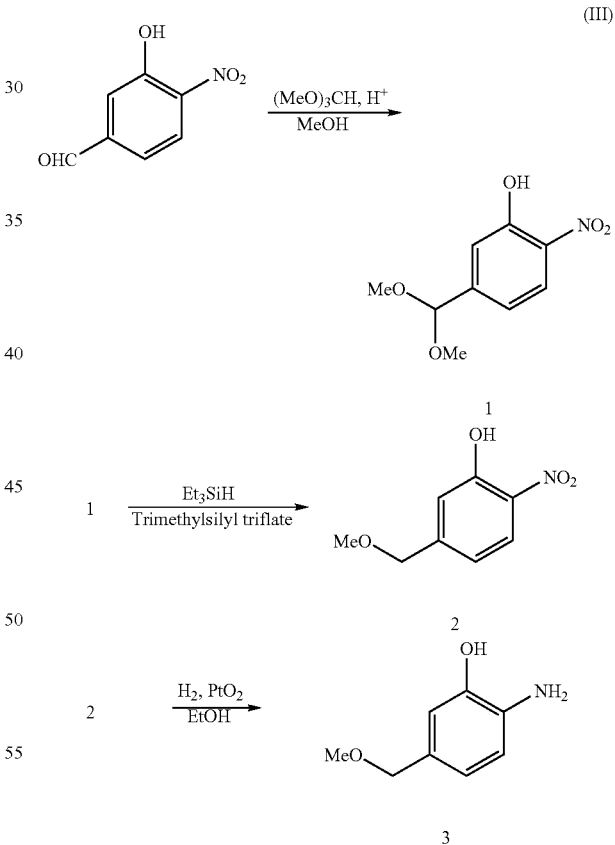

Procedure:

1. To obtain 3-Hydroxy-4-nitrobenzaldehyde, dimethyl acetal (1)

A mixture of 3-hydroxy-4-nitrobenzaldehyde (18 g, 106 mmol), trimethyl orthoformate (11 g, 12 mL, 106 mmol) and Nafion NR 50 resin (1.8 g) in $CH_2Cl_2$ (70 ml) and $CH_3OH$ (35 ml) was stirred and heated at 40° C. overnight. TLC (hexane-ether 10:1) indicated a complete reaction. The resin was filtered off, and the filtrate was concentrated in vacuo to an oil (22 g). The oil was purified on a column of silica gel (500 g) using hexane-ether (10:1) as the eluent. Fractions containing the product were concentrated in vacuo to yield 20 g (90%). The material was suitable for further transformation. The following $^1$H-Nuclear Magnetic Resonance (DMSO-$d_6$) values were measured: δ 10.98 (s, 1, OH); 7.88 (d,1,J=8.5 Hz); 7.16 (d,1,J=1.2 Hz); 6.97 (dd,1,J=1.4 Hz,8.5 Hz); 5.39 (s,1,CH); 3.26 (s,6,2×OMe).

2. To obtain 5-Methoxymethyl 2-Nitro phenol (2)

To a cooled (0° C.) solution of 1 (20 g, 96 mmol) and triethylsilane (12 g, 17 mL, 105 mmol) in $CH_2Cl_2$ (190 ml) was added trimethylsilyl trifluoromethane sulfonate (0.2 g, 1.2 mmol), and the solution was stirred at 0° C. for 0.5 hrs then allowed to warm to 20 °C and stirred overnight. The solution was poured into aqueous saturated sodium bicarbonate solution (275 mL) then extracted with ether (3×370 mL). The extracts were combined, dried ($MgSO_4$) then concentrated in vacuo to a solid (30 g). This solid was chromatographed on a column of silica gel (1.2 kg), packed in and eluted with hexane-ether (10:1). Fractions containing pure product were combined then concentrated to a yellow solid 20 g (89%) m.p. 52–53° C. (uncorrected). The material was suitable for further transformation. The following $^1$H-Nuclear Magnetic Resonance (DMSO-$d_6$) values were measured: δ 10.89 (s,1,OH); 7.87 (d, 1, J=8.5 Hz); 7.07 (s, 1); 6.89(d,1,J=8.5 Hz); 4.43 (s,2,$CH_2$); 3.32 (s,3,$CH_3$).

3. To obtain 2-amino-5-methoxymethyl-phenol (3)

A solution of 2 (20 g, 108 mmol) in EtOH (300 mL) was hydrogenated over $PtO_2$ (300 mg) in Parr pressure apparatus until the theoretical amount of hydrogen was absorbed. The catalyst was removed by filtration through a pad of Celite, and the filtrate was concentrated in vacuo to a solid (21 g, 100%). This solid was combined with material obtained from a smaller run then passed through a pad of silica gel (500 g) eluted with ether. Fractions containing pure product were combined, dried then concentrates, yield 20 g (89%) m.p. 108–108.5° C. (uncorrected).

Example 2

Synthesis of 2-amino-5-hydroxymethyl-phenol

This example shows how to make a preferred compound, which is suitable for use in the compositions of the invention, according to Reaction Sequence (IV):

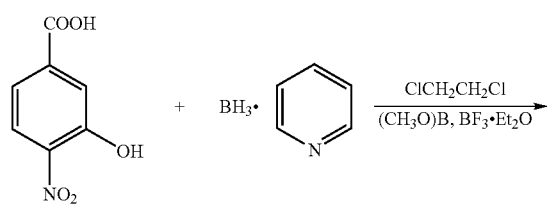

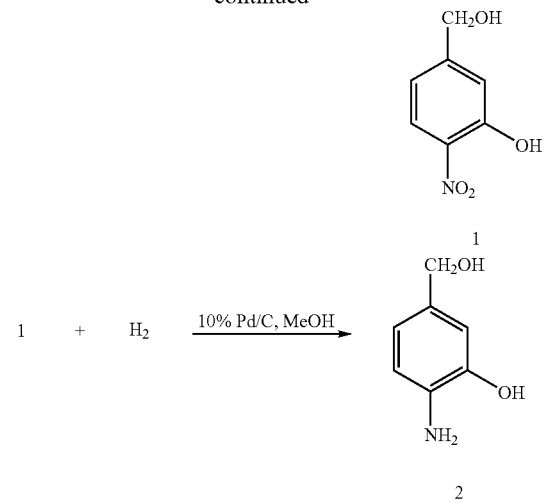

Procedure:

1. To obtain 5-Hydroxymethyl 2-Nitro phenol (1)

To a magnetically stirred suspension of 3-hydroxy-4-nitro-benzoic acid (75 g, 0.41 mol) in 1,2-dichloroethane (1.5 L), under an argon blanket, was added trimethyl borate (69 g, 0.66 mol) and boron trifluoride diethyl etherate (94 g, 0.66 mol) at 20 °C. Borane-pyridine complex (57 g, 0.61 mol) was slowly added drop-wise over 2.5 hrs (exotherm to 44° C.). After addition was complete, the solution was stirred for 2.5 hrs then cooled in an ice bath to 4° C. Methanol (150 ml) was added over 15–20 min. to quench the reaction. The mixture was stirred for 45 min. while warming to 20 °C then concentrated in vacuo to a yellow solid residue. The solid was partitioned between 1N NaOH (450 ml) and toluene (600 ml). The phases were separated, and the organic portion was extracted with 1N NaOH (2×450 mL). The aqueous portions were combined and acidified to below pH 2 with the slow addition of conc. HCl (100 ml). The resulting thick suspension was extracted with ethyl acetate (750 ml, 500 nm). The combined organic extract was washed with water (2×450 mL), brine (450 mL), dried ($MgSO_4$), filtered then concentrated in vacuo to give 62 g brownish yellow solid 1 (0.37 mol, 90%). An additional 106 g of intermediate 1 was obtained from three other reactions.

2. To obtain 2-amino-5-hydroxymethyl-phenol (2)

A 500 nm Parr bottle filled with argon was charged with 10% palladium on carbon catalyst (800 mg), methanol (240 mL) and compound 1(20 g, 0.12 mol). The mixture was placed on the hydrogenation apparatus, filled with hydrogen then shaken for 2 hrs until no further uptake of hydrogen was observed. The catalyst was removed by filtration through a Celite pad followed by several washes of the pad with methanol. The combined filtrate was concentrated in vacuo to give 17 g dark residue. The residue was suspended in warm (45° C.) ethyl acetate (100 mL) then cooled in an ice bath. The crystals that formed were collected by filtration, washed with a few portions of cold ethyl acetate then dried in vacuo at 45° C. to constant weight to give 12 g crystalline solid (72%). Additional reactions were carried out to give a total of 61 g of purified compound 2: m.p. 120–121° C. (uncorrected).

TABLE 3

Examples 3 to 12, which illustrate the inventive hair dyeing compositions, may be formulated as thickened, aqueous solutions, by conventional methods. A suitable procedure is described below.

| Ingredient | 3 | 4 | 5 | 6 | 7 | 8 | 9 | 10 | 11 | 12 |
|---|---|---|---|---|---|---|---|---|---|---|
| Sodium Sulphite | — | — | 0.1 | 0.1 | 0.1 | 0.1 | 0.1 | 0.3 | 0.1 | — |
| Ascorbic Acid | 0.5 | 0.1 | — | 0.1 | 0.3 | — | 0.6 | 0.1 | 0.1 | 0.2 |
| Ammonium Hydroxide | 6 | 8 | 8 | 7 | 8 | 9 | 10 | 8 | 8 | 10 |
| Ethylenediamedisuccinic acid | — | — | 1 | — | 1 | — | — | 0.5 | — | 1.5 |
| Oleth 5 | 1 | 2 | 3 | 0.5 | 1 | 1.5 | — | 0.8 | 2 | 1 |
| Oleth 2 | 0.8 | — | 0.8 | 0.8 | 1.5 | 2 | 0.8 | 0.5 | 0.8 | 2.5 |
| Oleic Acid | 0.9 | 1 | — | 0.3 | — | 0.9 | 0.9 | 0.8 | 1.1 | 0.9 |
| Soytrimonium chloride | 7 | 6 | 6 | 7 | 7 | — | — | 8 | 5 | 7 |
| Cocamide DEA | 3 | 1 | 1 | 3 | 0.5 | 0.8 | — | — | 3 | 2 |
| EDTA (Na$_4$ salt) | 0.1 | 0.1 | 0.1 | 0.1 | 0.1 | — | 0.1 | 0.1 | 0.1 | 0.1 |
| 1,4 diaminobenzene | 0.8 | 0.5 | — | 0.5 | 0.8 | — | 0.5 | 0.6 | 0.5 | 0.8 |
| 4-aminophenol | 0.2 | — | — | 0.1 | 0.2 | — | — | 0.2 | 0.1 | 0.2 |
| 3-aminophenol | 0.5 | 0.5 | — | 0.6 | 1 | — | 0.5 | 1 | 0.6 | 1 |
| 4-amino-3-methylphenol | 0.2 | — | — | 0.2 | 0.2 | — | 1 | — | 0.2 | 0.3 |
| 2-(4,5-diamino-1H-pyrazol-1-yl)ethanol | — | 0.5 | — | — | 0.5 | — | 0.5 | 1 | — | 0.3 |
| N,N-Bis(2-hydroxyethyl)-p-phenylenediamine | — | 0.4 | — | 1 | 0.2 | — | 0.2 | — | 0.2 | 0.3 |
| 2-aminophenol | 1 | 1 | — | — | — | — | — | — | — | — |
| 5-methyl-2-aminophenol | — | — | — | 1 | — | — | — | — | — | — |
| 5-methoxymethyl 2-aminophenol | 1 | 0.5 | — | — | 1 | 1.5 | 1 | — | — | — |
| 5-hydroxymethyl 2-aminophenol | — | — | 1 | 0.8 | — | — | — | 1 | 1 | 1 |
| Propylene Glycol | 8.2 | 8 | 7.8 | 8.2 | 8.4 | 8 | 8.2 | 8.2 | 7.8 | 8.2 |
| Hexylene Glycol | 8 | 7 | 8 | 6 | 8 | 8 | — | 9 | 8 | 9 |
| Ethoxy Diglycol | 4.2 | 4 | 4.6 | 4.2 | 4.2 | 5 | 4.2 | 3 | 4.2 | 4.2 |
| Water | qs | qs | qs | qs | qs | qs | qs | qs | qs | qs |

To prepare pre-mix: Add to a suitable vessel in the following order, citric acid, ethoxy diglycol, oleic acid, propylene glycol, and cocaamidopropyl betaine, then agitate until fully dispersed, then add Oleth-10, Oleth-2 and acrylate co-polymers, continue the agitation for 10 minutes and transfer to main vessel. To the main vessel then add water (heated to 50° C.), oleic acid, water, sodium sulphite, and EDTA. Next weigh out and add the ascorbic acid, then stir well until dissolved. Separately weigh dyes into a clean beaker and transfer also to the main vessel. Add the dyes and stir until dissolved (heat to 40° C. as necessary). Cool to room temperature with stirring, add the ammonium hydroxide and water with stirring, add citric acid to pH 10, and transfer to the storage container.

TABLE 4

Examples 13 to 22, which illustrate the inventive hair dyeing compositions, may be formulated as emulsions, by conventional methods. The procedure described for Examples 3 to 12 is suitable.

| Ingredient | 13 | 14 | 15 | 16 | 17 | 18 | 19 | 20 | 21 | 22 |
|---|---|---|---|---|---|---|---|---|---|---|
| Sodium Sulphite | — | — | 0.1 | 0.1 | 0.1 | 0.1 | 0.1 | 0.3 | 0.1 | — |
| Ascorbic Acid | 0.5 | 0.1 | — | 0.1 | 0.3 | — | 0.6 | 0.1 | 0.1 | 0.2 |
| Ammonium Carbonate | 3 | 6 | 2 | — | 4 | 8 | 2 | — | 4 | 6 |
| Potassium Hydrogen Carbonate | — | — | 1.5 | 2 | — | — | 2 | 2 | — | — |
| Ammonium Acetate | — | — | — | 2 | — | — | — | 2 | — | — |
| Ceteareth 25 | 1 | — | 1.5 | 1 | 1 | 2 | 1 | 1 | — | 1 |
| Cetyl Alcohol | 1.6 | 1.2 | 1.6 | 1.6 | — | 1.8 | 1.6 | 1.6 | 2 | 1.6 |
| Stearyl Alcohol | 3.3 | — | 3.3 | 3 | 3.3 | 2.5 | 3.3 | 4 | 3.3 | — |
| Sodium Benzoate | 0.1 | 0.1 | 0.1 | 0.1 | 0.1 | 0.1 | 0.1 | 0.1 | 0.1 | 0.1 |
| Phenoxyethanol | 0.1 | 0.1 | 0.1 | 0.1 | 0.1 | 0.1 | 0.1 | 0.1 | 0.1 | 0.1 |
| EDTA (Na$_4$ salt) | 0.1 | 0.1 | 0.1 | 0.1 | 0.1 | 0.1 | 0.1 | 0.1 | 0.1 | 0.1 |
| Sodium Glycinate | 2 | 5 | 3 | 1 | — | — | — | — | — | 3 |
| Glutamic Acid | — | — | — | 2 | 2 | 6 | 2 | — | — | — |
| Glucosamine | — | — | — | — | — | — | 2 | 4 | 4 | 3 |
| 1,4 diaminobenzene | 0.8 | 0.5 | 0.6 | — | 0.8 | 0.8 | 0.5 | 0.6 | — | 0.8 |
| 4-aminophenol | 0.2 | 0.3 | 0.2 | — | 0.2 | 0.2 | 0.3 | 0.2 | — | 0.2 |
| 3-aminophenol | 1 | 0.5 | 1 | — | 1 | 1 | 0.5 | 1 | — | 1 |
| 1,3 dihydroxybenzene | 1.6 | 1.2 | 1.6 | — | 1.6 | 1.6 | 1.2 | 1.6 | — | 1.6 |
| 4-amino-3-methylphenol | 0.2 | — | — | 0.2 | 0.2 | — | 1 | — | 0.2 | 0.3 |
| 2-(4,5-diamino-1H-pyrazol-1-yl)ethanol | — | 0.5 | — | — | 0.5 | — | 0.5 | 1 | — | 0.3 |
| N,N-Bis(2-hydroxyethyl)-p-phenylenediamine | — | 0.4 | — | 1 | 0.2 | — | 0.2 | — | 0.2 | 0.3 |
| 2-aminophenol | 1 | 1 | — | — | — | — | — | — | — | — |
| 5-methyl-2-aminophenol | — | — | 1 | 1 | — | — | — | — | — | — |
| 5-methoxymethyl 2-aminophenol | 1 | 1 | 1 | 1 | 1 | 1 | 1 | — | — | — |
| 5-hydroxymethyl 2-aminophenol | — | 1 | 1 | — | — | — | — | 1 | 1 | 1 |
| pH adjust to pH 9.0 | qs | qs | qs | qs | qs | qs | qs | qs | qs | qs |
| Water | qs | qs | qs | qs | qs | qs | qs | qs | qs | qs |

TABLE 5

Examples 23 to 32, which illustrate the inventive hair dyeing compositions, may be formulated as emulsions, by conventional methods. The procedure described for Examples 3 to 12 is suitable.

| Ingredient | 23 | 24 | 25 | 26 | 27 | 28 | 29 | 30 | 31 | 32 |
|---|---|---|---|---|---|---|---|---|---|---|
| Sodium Sulphite | — | — | 0.1 | 0.1 | 0.1 | 0.1 | 0.1 | 0.3 | 0.1 | — |
| Ascorbic Acid | 0.5 | 0.1 | — | 0.1 | 0.3 | — | 0.6 | 0.1 | 0.1 | 0.2 |
| Ammonium Carbonate | 3 | 6 | 2 | — | 4 | 8 | 2 | — | 4 | 6 |
| Potassium Hydrogen Carbonate | — | — | 1.5 | 2 | — | — | 2 | 2 | — | — |
| Ammonium Acetate | — | — | — | 2 | — | — | — | 2 | — | — |
| Blended phosphate thickener[1] | 3 | 2 | 1.5 | 4 | 3 | 1 | 1.8 | 2 | 3 | 3 |
| EDTA (Na$_4$ salt) | 0.1 | 0.1 | 0.1 | 0.1 | 0.1 | 0.1 | 0.1 | 0.1 | 0.1 | 0.1 |
| Sodium Glycinate | 2 | 5 | 3 | 1 | — | — | — | — | — | 3 |
| Glutamic Acid | — | — | — | 2 | 2 | 6 | 2 | — | — | — |
| Glucosamine | — | — | — | — | — | — | 2 | 4 | 4 | 3 |
| 1,4 diaminobenzene | 0.8 | — | 0.6 | 0.5 | 0.8 | 0.8 | 0.5 | 0.6 | — | 0.8 |
| 4-aminophenol | 0.2 | — | 0.2 | 0.1 | 0.2 | 0.2 | 0.3 | 0.2 | — | 0.2 |
| 3-aminophenol | 1 | — | 1 | 0.6 | 1 | 1 | 0.5 | 1 | — | 1 |
| 1,3 dihydroxybenzene | 1.6 | — | 1.6 | 0.8 | 1.6 | 1.6 | 1.2 | 1.6 | — | 1.6 |
| 4-amino-3-methylphenol | 0.2 | — | — | 0.2 | 0.2 | — | 1 | — | 0.2 | 0.3 |
| 2-(4,5-diamino-1H-pyrazol-1-yl)ethanol | — | 0.5 | — | — | 0.5 | — | 0.5 | 1 | — | 0.3 |
| N,N-Bis(2-hydroxyethyl)-p-phenylenediamine | — | 0.4 | — | 1 | 0.2 | — | 0.2 | — | 0.2 | 0.3 |
| 2-aminophenol | 1 | — | — | — | — | — | — | — | — | — |
| 5-methyl-2-aminophenol | — | — | 1 | 1 | — | — | — | — | — | — |
| 5-methoxymethyl 2-aminophenol | 1 | 1 | — | — | 1 | 1 | 1 | — | — | — |
| 5-hydroxymethyl 2-aminophenol | — | — | 1 | — | — | — | — | 1 | 1 | 1 |
| pH adjust to pH 9.0 | qs | qs | qs | qs | qs | qs | qs | qs | qs | qs |
| Water | qs | qs | qs | qs | qs | qs | qs | qs | qs | qs |

[1]Ceteth-10 phosphate/di-cetyl phosphate/cetearyl alcohol blend, available as CRODAFOS (TM) CES, from Croda (United Kingdom).

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A compound is selected from the group consisting of:

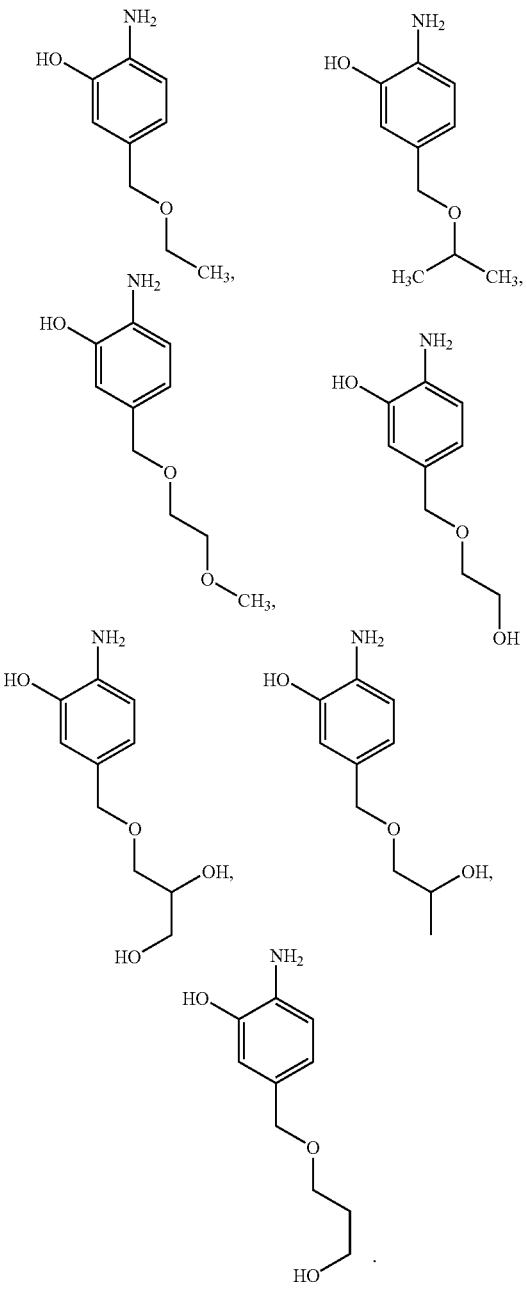

2. A compound according to claim 1, wherein said compound is selected from the group consisting of:

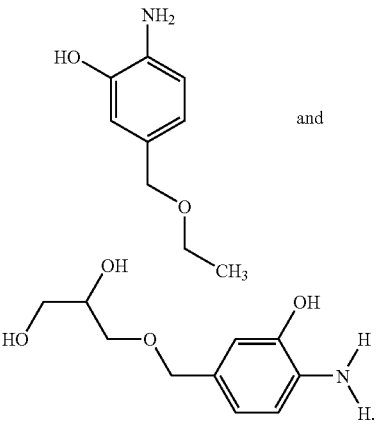

3. A composition for the oxidative dyeing of keratin fibers, comprising a medium suitable for dyeing and a compound of the formula (II), or its salts with an inorganic or organic acid,

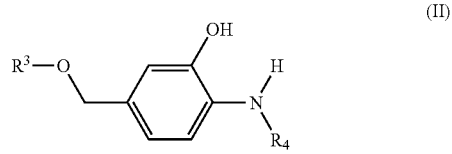

wherein $R^3$ is monovalent and is selected from: (a) substituted or unsubstituted, straight or branched, alkyl, mono- or poly-unsaturated alkyl, heteroalkyl, aliphatic, heteroaliphatic, or heteroolefinic systems, (b) substituted or unsubstituted, mono- or poly-cyclic aliphatic, aryl, or heterocyclic systems, (c) substituted or unsubstituted, mono-, poly-, or per-fluoro alkyl systems; said systems of (a), (b) and (c) comprising from about 1 to about 12 carbon atoms and about 0 to about 5 heteroatoms selected from O, S, N, P, and Si; and wherein $R^4$ is monovalent and is selected from: (a), (b) and (c) herein, or H.

4. A composition according to claim 3, wherein $R^3$ is monovalent and is selected from: (a) substituted or unsubstituted, straight or branched, alkyl, heteroalkyl, aliphatic, heteroaliphatic, or heteroolefinic systems, (b) substituted or unsubstituted, mono- or poly-cyclic aliphatic, aryl or heterocyclic systems, c) substituted or unsubstituted, mono-, poly-, or per-fluoro alkyl systems; said systems of (a), (b) and (c) comprising from about 1 to about 8 carbon atoms and about 0 to about 3 heteroatoms selected from O, S, and N; and wherein $R^4$ is monovalent and is selected from: (a), (b) and (c) herein, or H.

5. A composition according to claim 4, wherein $R^3$ is monovalent and is selected from: (a) substituted or unsubstituted, straight or branched, alkyl, heteroalkyl, aliphatic, or heteroaliphatic systems, (b) substituted or unsubstituted, aryl, or heterocyclic (c) substituted or unsubstituted, mono-, poly-, or per-fluoro alkyl systems; said systems of (a), (b) and (c) comprising from about 1 to about 6 carbon atoms and about 0 to about 2 heteroatoms selected from O, and N; and wherein R⁴ is monovalent and is selected from: (a), (b) and (c) herein, or H.

6. A composition according to claim 5, wherein R⁴ is H; and
wherein R³ is selected from: substituted or unsubstituted, straight or branched, alkyl, or heteroalkyl systems; said systems comprising from about 1 to about 4 carbon atoms and about 0 to about 1 oxygen atoms.

7. A composition according to claim 5, wherein R³ is, selected from the group consisting of: (a) a straight or branched $C_1$–$C_4$ alkyl radical; (b) a phenyl ring (c) a benzyl radical; (d) a heterocyclic radical having a 5- or 6-membered ring, (e) a substituted or unsubstituted, mono-, poly-, or per-fluoro alkyl systems; said systems comprising from 1 to 4 carbon atoms; (f) a —($CH_2$—$CH_2$—O)$_p$-OR' radical, wherein p is an integer from 1 to 3, wherein R' is H, or a $C_1$–$C_4$ alkyl radical; (g) a —($CH_2$—CH($CH_3$))$_q$-OR' radical, wherein q is an integer from 1 to 2, wherein R' is H, or a $C_1$—$C_4$ alkyl radical; and
wherein R⁴ is selected from: (a), (b), (c), (d), (e), (f), and (g) herein, or H.

8. A composition according to claim 7, wherein R⁴ is H; and
wherein R³ is selected from the group consisting of: (a) an alkyl radical selected from methyl, ethyl, isopropyl and tert-butyl radicals; (b) a phenyl radical; (c) a benzyl radical; (d) a heterocyclic radical selected from a thiophene ring, a furan ring, a pyrazole ring, a pyrimidine ring, and a pyridine ring; (e) a trifluoromethyl radical; and (f) an alkoxyethyl radical selected from methoxyethyl, ethoxyethyl, and isopropoxyethyl radicals.

9. A composition according to claim 8, wherein said compound is selected from the group consisting of:

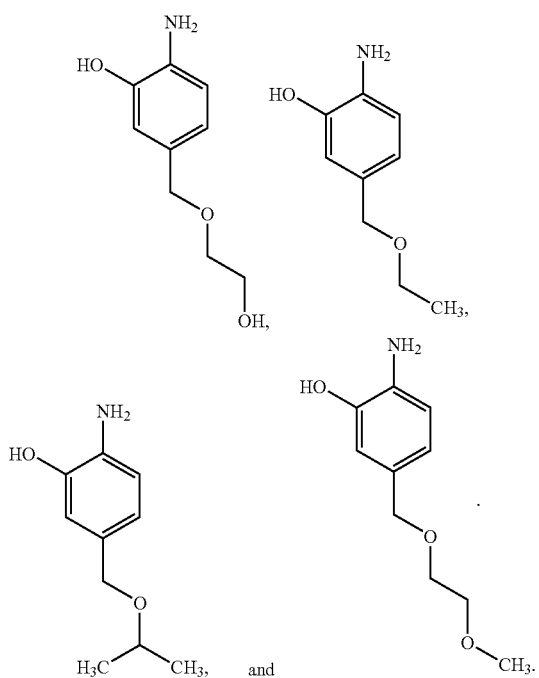

10. A composition according to claim 9, wherein said compound is selected from the group consisting of:

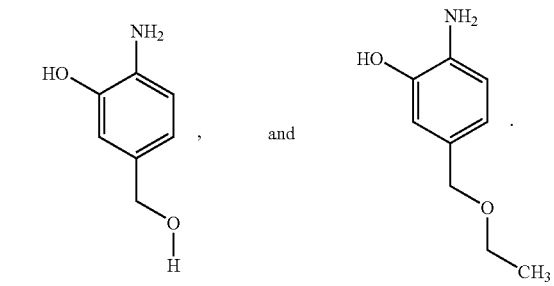

11. A composition according to claim 10, wherein said compound is:

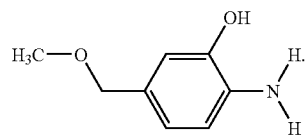

12. A composition according to claim 3, wherein at least one of R³ and R⁴ is substituted, the substituent being selected from:
(a) the group of C-linked monovalent substituents consisting of: (i) substituted or unsubstituted, straight or branched, alkyl, mono- or poly-unsaturated alkyl, heteroalkyl, aliphatic, heteroaliphatic, or heteroolefinic systems, (ii) substituted or unsubstituted, mono- or poly-cyclic aliphatic, aryl, or heterocyclic systems, or (iii) substituted or unsubstituted, mono-, poly-, or per-fluoro alkyl systems; said systems of (i), (ii) and (iii) comprising from about 1 to about 10 carbon atoms and about 0 to about 5 heteroatoms selected from O, S, N, P, and Si;
(b) the group of S-linked monovalent substituents consisting of SA¹, SCN, $SO_2A^1$, $SO_3A^1$, SSA¹, SOA¹, $SO_2NA^1A^2$, SNA¹A², and SONA¹A²;
(c) the group of O-linked monovalent substituents consisting of OA¹, OCN and ONA¹A²:
(d) the group of N-linked monovalent substituents consisting of NA¹A², (NA¹A²A³)⁺, NC, NA¹OA², NA¹SA², NCO, NCS, $NO_2$, N=NA¹, N=NOA¹, NA¹CN, NA¹NA²A³;
(e) the group of monovalent substituents consisting of COOA¹, $CON_3$, $CONA^1_2$, CONA¹COA², C(=NA¹)NA¹A, CHO, CHS, CN, NC, and X; and
(f) the group consisting fluoroalkyl monovalent substituents consisting of mono-, poly-, or per-fluoro alkyl systems comprising from about 1 to about 12 carbon atoms and about 0 to about 4 heteroatoms;
wherein A¹, A², and A³ are monovalent and are independently selected from: (1) H, (2) substituted or unsubstituted, straight or branched, alkyl, mono- or poly-unsaturated alkyl, heteroalkyl, aliphatic, heteroaliphatic, or heteroolefinic systems, (3) substituted or unsubstituted, mono- or poly-cyclic aliphatic, aryl, or heterocyclic systems, or (4) substituted or unsubstituted, mono-, poly-, or per-fluoro alkyl systems; said systems of (2), (3) and (4) comprising from about 1 to about 10 carbon atoms and about 0 to about 5 heteroatoms selected from O, S, N, P, and Si; and wherein X is a halogen selected from the group consisting of F, Cl, Br, and I.

13. A composition according to claim 12, wherein R³ and R⁴, are selected from the group consisting of: (a) a phenyl ring substituted by X, a $C_1$–$C_4$ alkyl radical, a $C_1$–$C_4$ alkoxy radical, an amino radical, a trifluoromethyl radical, or a $C_1$–$C_4$ alkylamino radical; (b) a benzyl radical substituted by X, a $C_1$–$C_4$ alkyl radical, a $C_1$–$C_4$ alkoxy radical, a nitro radical, an amino radical, a trifluoromethyl radical, or a $C_1$–$C_4$ alkylamino radical; (c) a $C_1$–$C_8$ mono-, di-, or tri-hydroxyalkyl radical; (d) a $C_1$–$C_4$ aminoalkyl radical; (e) a $C_1$–$C_8$ N-alkylaminoalkyl radical; (f) a $C_1$–$C_{12}$ N,N-dialkylaminoalkyl radical; (g) an arylaminoalkyl radical; (h) a $C_1$–$C_8$ alkoxyalkyl radical selected from methoxyalkyl, ethoxyalkyl and phenoxyalkyl; (i) a $C_1$–$C_4$ haloalkyl radical selected from bromoalkyl, chloroalkyl and fluoroalkyl; (j) a $C_1$–$C_4$ carboxyalkyl group; (k) a $C_1$–$C_8$ alkoxycarbonylalkyl radical; (l) a phenyloxycarbonylalkyl radical; (m) a $C_1$–$C_4$ methanesulphonylalkyl radical; (n) a $C_1$–$C_4$ cyanoalkyl radical; (o) an N,N-di(hydroxyalkyl)aminoalkyl radical; and (p) an N-hydroxyalkylaminoalkyl radical.

14. A composition according to claim 12, wherein $R^4$ is H, and wherein $R^3$ is selected from the group consisting of: (a) a toluyl radical; (b) a 4-chlorophenlyl radical; (c) a 4-methoxyphenyl radical; (d) a 3-methoxyphenyl radical) (e) a 2-methoxyphenyl radical; (f) a hydroxyethyl radical; (g) an aminoethyl radical; (h) a dihydroxyethyl radical; (i) a dihydroxypropyl radical; (j) a hydroxypropyl radical; (k) a hydroxybutyl radical; (l) an N-methylaminomethyl radical; (m) an N,N-dimethylaminomethyl radical; (n) an N-methylaminomethyl radical; (o) an N,N-dimethylaminomethyl radical; (p) an N-methylaminomethyl radical; (q) an N,N-dimethylaminomethyl radical; (r) an N-ethylaminomethyl radical; (s) an N,N-dimethylaminomethyl radical; (t) a carboxyethyl radical; (u) a carboxymethyl radical; (v) a methoxycarbonylethyl radical; (w) a methoxycarbonylmethyl radical; (x) an ethoxycarbonylethyl radical; (y) an ethoxycarbonylmethyl radical; (z) a cyanomethyl radical; and (aa) a cyanoethyl radical.

15. A composition according to claim 14, wherein said compound is selected from the group consisting of:

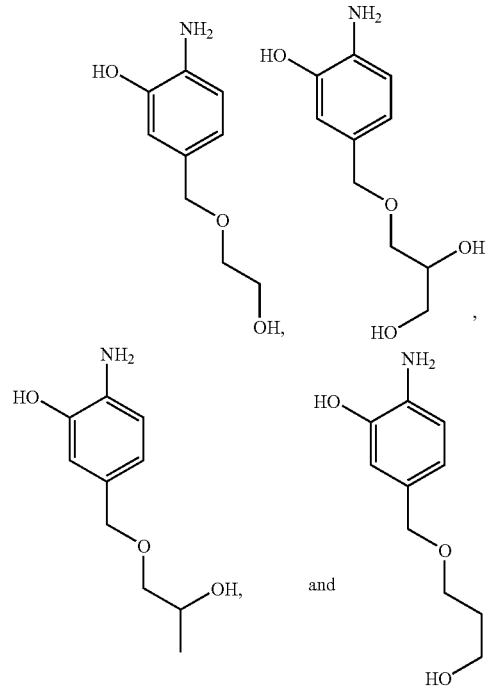

16. A composition according to claim 15, wherein said compound is selected from the group consisting of:

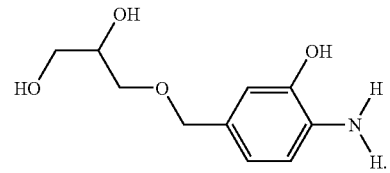

17. A composition according to claim 3, wherein in said compound at least one of $R^3$ and $R^4$ is substituted, the substituent having a Hammett Sigma Pars Value from about −0.65 to about +0.75.

18. A composition according to claim 17, wherein the substituent has a Hammett Sigma Para Value from about −0.4 to about +0.5.

19. A composition according to claim 3, wherein in said compound at least one of $R^3$ and $R^4$ is substituted, and the compound has a negative log D at pH10.

20. A composition according to claim 3, wherein in said compound at least one of $R^3$ and $R^4$ is substituted, and the compound has a log D at pH 10 such that the absolute value of the difference between the log D of the compound and the log D of the same compound with H replacing the substituent or substituents is greater than 0.5.

21. A composition according to claim 3, wherein in said compound at least one of $R^3$ and $R^4$ is substituted, the substituent comprising at least one —OH group.

22. A composition according to claim 3, comprising from about 0.001% to about 10% of said compound, by weight of the composition.

23. A composition according to claim 22, comprising from about 0.01% to about 5% of said compound, by weight, of the composition.

24. A composition according to claim 3, wherein said medium comprises a solvent selected from the group consisting of water, ethanol, propanol, isopropanol, glycerol, 1,2-propylene glycol, hexylene glycol, ethoxy diglycol, and mixtures thereof.

25. A composition according to claim 3, further comprising a surfactant selected from the group consisting of anionic, cationic, nonionic, amphoteric or zwitterionic surfactants, and mixtures thereof.

26. A composition according to claim 3, further comprising a primary intermediate selected from p-phenylenediamine, p-aminophenol, o-phenylenediamine, o-aminophenol, heterocyclics, derivatives thereof, and mixtures thereof.

27. A composition according to claim 26, wherein said p-phenylenediamine derivatives are selected from the group consisting of: 2-methyl-benzene-1,4-diamine; benzene-1,4-diamine; 1-(2,5-diamino-phenyl)-ethanol; 2(2,5-diamino-phenyl)-ethanol; N-(2-methoxyethyl)benzene-1,4-diamine; 2-[(4-amino-phenyl)-(2hydroxy-ethyl)-amino]-ethanol; 1-(2,5-diaminophenyl)ethane-1,2-diol; 1-(2'-Hydroxyethyl)-2,5-diaminobenzene; 1,3-Bis (N(2-Hydroxyethyl)-N-(4-amino-phenyl)amino)-2-propanol; 2,2'-[1,2-Ethanediyl-bis-(oxy-2,1-ethanediyloxy)]-bis-benzene-1,4-diamine; N,N-Bis(2-hydroxyethyl)-p-phenylenediamine; and mixtures thereof.

28. A composition according to claim 26, wherein said p-aminophenol derivatives are selected from the group consisting of: 4-amino-phenol, 4-methylamino-phenol, 4-amino-3-methyl-phenol, 4-amino-2-methoxymethyl-phenol; 1-(5-amino-2-hydroxy-phenyl)-ethane-1,2-diol; 1-Hydroxy-2,4-diaminobenzene; 1-(2'-Hydroxyethyloxy)-2,4-diaminobenzene; 4-Amino-2-aminomethylphenol; 2,4-Diamino-5-methylphenetol; 4-Amino-1-hydroxy-2-(2'-hydroxyethylaminomethyl)benzene; 1-methoxy-2-amino-4-(2'hydroxyethylamino)benzene; 5-aminosalicylic acid and salts thereof; and mixtures thereof.

29. A composition according to claim 26, wherein said o-phenylenediamine derivatives are selected from the group consisting of; 3,4-Diaminobenzoic acid and salts thereof.

30. A composition according to claim 26, wherein said o-aminophenol derivatives are selected from the group consisting of: 2-amino-phenol, 2-amino-5-methyl-phenol, 2-amino-6-methyl-phenol, N-(4-amino-3-hydroxy-phenyl)-acetamide; 2-amino-4-methyl-phenol; and mixtures thereof.

31. A composition according to claim 26, wherein said heterocyclic derivatives are selected from the group consisting of: pyrimidine-2,4,5,6-tetramine; 1-methyl-1H-pyrazole-4,5-diamine;2-(4,5-diamino-1H-pyrazol-1-yl)ethanol; 1-(4-methylbenzyl)-1H-pyrazole-4,5-diamine; 1-(benzyl)-1H-pyrazole-4,5-diamine; $N^2,N^2$-dimethyl-pyridine-2,5-diamine; 4-Hydroxy-2,5,6-triaminopyrimidine; 1-(2'hydroxyethyl)-amino-3,4-methylene dioxybenzene; and 1-Hydroxyethyl-4,5-diaminopyrazole sulphate; and mixtures thereof.

32. A composition according to claim 26, wherein said primary intermediate is selected from the group consisting of: 2-methyl-benzene-1,4-diamine; benzene-1,4-diamine; N,N-Bis(2-hydroxyethyl)-p-phenylenediamine; 4-aminophenol; 4-methylamino-phenol; 4-amino-3-methyl-phenol; 1-Hydroxy-2,4-diaminobenzene; 2-amino-phenol; 2-amino-5-methyl-phenol; 2-amino-6-methyl-phenol; 1-methyl-1H-pyrazole-4,5-diamine; 1-Hydroxyethyl-4,5-diaminopyrazole sulphate; 2-(4,5-diamino-1H-pyrazol-1-yl) ethanol; and mixtures thereof.

33. A composition according to claim 3, further comprising a coupler selected from phenol, resorcinol, naphthol, m-phenylenediamine, m-aminophenol, heterocyclics, derivatives thereof, and mixtures thereof.

34. A composition according to claim 33, wherein said phenol, resorcinol, and naphthol derivatives are selected from the group consisting of: naphthalene-1,7-diol, benzene-1,3-diol, 4-chlorobenzene-1,3-diol, naphthalen-1-ol, 2-methyl-naphthalen-1-ol, naphthalene- 1,5-diol, naphthalene-2,7-diol, benzene- 1,4-diol, 2-methyl-benzene- 1,3-diol, and 2-isopropyl-5-methylphenol; 1,2,4-Trihydroxy-benzene; 1-Acetoxy-2-methylnaphthalene; and mixtures thereof.

35. A composition according to claim 33, wherein said m-phenylenediamine derivatives are selected from the group consisting of: benzene-1,3-diamine, 2-(2,4-diamino-phenoxy)-ethanol, 4-{3-[(2,4-diaminophenyl) oxy] propoxy}benzene-1,3-diamine, 2-(3-amino-4-methoxy-phenylamino)-ethanol, 2[2,4-diamino-5-(2-hydroxy-ethoxy)-phenoxy]-ethanol, and 3-(2,4-diamino-phenoxy)-propan-1-ol; 2,4-Diamino-5-(2'-hydroxythyloxy)toluene; N,N-Dimethyl-3-ureidoaniline; 2,4-Diamino-5-fluorotoluenesulfatehydrate; 1-methyl-2,6-bis (2-hydroxyethylamino)benzene; and mixtures thereof.

36. A composition according to claim 33, wherein said m-aminophenol derivatives are selected from the group consisting of: 3-amino-phenol, 5-amino-2-methyl-phenol, 5-(2-hydroxy-ethylamino)-2-methyl-phenol, and 3-amino-2-methyl-phenol; 1-Methyl-2-hydroxy-4-(2'-hydroxyethyl) aminobenzene; 1-Hydroxy-3-amino-2,4-dichlorobenzene; 1,3-Bis-(2,4-Diaminophenoxy)propane; 1-Hydroxy-2-methyl-5-amino-6-chlorobenzene; 5-Amino-4-chloro-2-methylphenol; and mixtures thereof.

37. A composition according to claim 33, wherein said heterocyclic derivatives are selected from the group consisting of: 3,4-dihydro-2H-1,4-benzoxazin-6-ol, 4-methyl-2-phenyl-2,4-dihydro-3H-pyrazol-3-one, 1,3-benzodioxol-5-ol, 1,3-benzodioxol-5-amine, 1H-indol 4-ol 1H-indole-5,6-diol, 1H-indol-7-ol, 1H-indol-5-ol, 1H-indol-6-ol, 1H-indole-2,3-dione, pyridine-2,6-diamine, 2-aminopyridin-3-ol, 4-hydroxy-N-methylindole, 1H-5-methylpyrazol-5-one, 1-phenyl-3-methylpyrazol-5-one, 2,6-dimethylpyrazolo[1,5-b]-1,2,4-triazole, 2,6-dimethyl[3,2-c]1,2,4-triazole, 6-methylpyrazolo-[1,5-a]benzimidazole; 2,6-dihydroxypyridine; 2,6-dihydroxy-3,4-dimethylpyridine; 6-Hydroxybenzomorpholine; 2,6-Dihydroxy-3,4-dimethylpyridine; 3,5-Diamino-2,6-dimethoxypyridine; 3-Amino-2-methylamino-6-methoxypyridine; 1-Phenyl-3-methyl-5-pyrazolone-2,4-dihydro-5,2-phenyl-3H-pyrazole-3-one; and mixtures thereof.

38. A composition according to claim 33, wherein said coupler is selected from the group consisting of benzene-1,3-diol; 4-chlorobenzene-1,3-diol; 2-methyl-benzene-1,3-diol; benzene-1,3-diamine; 3-amino-phenol; 5-amino-2-methyl-phenol; 1-Methyl-2-hydroxy-4-(2'-hydroxyethyl) aminobenzene; 4-methyl-2-phenyl-2,4-dihydro-3H-pyrazol-3-one; 2-aminopyridin-3-ol; 1-phenyl-3-methylpyrazol-5-one; 1-Phenyl-3-methyl-5-pyrazolone-2,4-dihydro-5,2-phenyl 3H-pyrazole-3-one; and mixtures thereof.

39. A composition according to claim 3, further comprising a primary intermediate and coupler combination selected from the group consisting of: (a) resorcinol, 4-amino-m-cresol, 2-methylresorcinol, 4-amino-2-hydroxytoluene, m-aminophenol and 2-amino-4-hydroxyethyl anisole sulphate; (b) resorcinol, 4-amino-m-cresol, 2-methylresorcinol, 4-amino-2-hydroxytoluene, m-aminophenol, 2-amino-4-hydroxyethyl anisole sulphate, 1-napthol and toluene-2,5-diamine; (c) 2-methyl-5-hydroxyethylaminophenol, resorcinol, toluene-2,5-diamine, m-aminophenol, p-aminophenol and p-methylaminophenol; (d) 2-methyl-5-hydroxyethylaminophenol, m-aminophenol, p-aminophenol, p-methylaminophenol and p-phenylenediamine; (e) 1-hydroxyethyl-4,5-diamino pyrazole sulphate and m-aminophenol; and (f) 2-methylresorcinol, p-aminophenol, 4-amino-2-hydroxytoluene, p-phenylenediamine and N,N-Bis(2-hydroxyethyl)-p-phenylenediamine.

40. A composition according to claim 3, further comprising a direct dye.

41. A composition according to claim 40, wherein said direct dye is selected from the group consisting of: Disperse Black 9, HC Yellow 2, HC Yellow 4, HC Yellow 15, 4-nitro-o-phenylenediamine, 2-amino-6-chloro-4-nitrophenol, HC Red 3, Disperse Violet 1, HC Blue. 2, Disperse Blue 3, Disperse Blue 377, Basic Red 51, Basic Orange 31, Basic Yellow 87, and mixtures thereof.

42. A composition according to claim 3, further comprising an oxidizing agent selected from the group consisting of: hydrogen peroxide; inorganic alkali metal peroxides; organic peroxides; inorganic perhydrate salt bleaching compounds; alkali metal bromates; enzymes; and mixtures thereof.

43. A composition according to claim 42, wherein said oxidizing agent is selected from the group consisting of: hydrogen peroxide; sodium periodate; sodium peroxide; urea peroxide; sodium perborate; sodium percarbonate; sodium perphosphate; sodium persilicate; sodium persulphate; and mixtures thereof.

44. A composition according to claim 43, wherein said oxidizing agent is hydrogen peroxide.

45. A composition according to claim 3, further comprising a thickener.

46. A composition according to claim 45, wherein said thickener is a salt tolerant thickeners selected from the group consisting of: xanthan, guar, hydroxypropyl guar, ethyl cellulose, hydroxyethyl cellulose, hydroxypropyl cellulose, N-vinylpyrollidone, Acrylates/Ceteth-20 Itaconate copolymer, PEG-150/Decyl/SMDI copolymer, PEG-150/Stearyl/SMDI copolymer, trihydroxystearin, Acrylates/Steareth-20 Methacrylate copolymer, blended Ceteth-10 phosphate/Dicetyl phosphate/Cetearyl alcohol, and mixtures thereof.

47. A composition according to claim 3, further comprising ethylenediaminedisuccinic acid (EDDS), or salts thereof.

48. A composition according to claim 3, further comprising a pH modifier selected from the group consisting of: ammonia, monoethanolamine, diethanolamine, triethanolamine, 2-amino-2-methyl-1-propanol, 2-amino-2-hydroxymethyl-1,3,-propandiol, sodium hydroxide, ammonium carbonate, phosphoric acid, acetic acid, ascorbic acid, citric acid, tartaric acid, hydrochloric acid, potassium hydroxide, and mixtures thereof.

49. A composition according to claim 3, further comprising a carbonate ion source and radical scavenger system.

50. A composition according to claim 49, wherein said carbonate ion source is selected from: sodium carbonate, sodium hydrogen carbonate, potassium carbonate, potassium hydrogen carbonate, guanidine carbonate, guanidine hydrogen carbonate, lithium carbonate, calcium carbonate, magnesium carbonate, barium carbonate, ammonium carbonate, ammonium hydrogen carbonate and mixtures thereof.

51. A composition according to claim 49, wherein said radical scavenger is selected from: monoethanolamine, 3-amino-1-propanol, 4-amino-1-butanol, 5-amino-1-pentanol, 1-amino-2-propanol, 1-amino-2-butanol, 1-amino-2-pentanol, 1-amino-3-pentanol, 1-amino-4-pentanol, 3-amino-2-methylpropan-1-ol, 1-amino-2-methylpropan-2-ol, 3-aminopropane-1,2-diol, glucosamine, N-acetylglucosamine, glycine, arginine, lysine, proline, glutamine, histidine, serine, tryptophan, and potassium, sodium and ammonium salts thereof, and benzylamine, glutamic acid, imidazole, di-tert-butylhydroxytoluene, hydroquinone, catechol, and mixtures thereof.

52. A composition according to claim 3, consisting of an aqueous or aqueous-alcoholic preparation in the form of a solution, cream or gel.

53. A method for oxidative dyeing of keratin fibers, comprising applying a composition according to claim 3 in the presence of an oxidizing agent, for a period which is sufficient to develop the desired coloration.

54. A method according to claim 53 wherein said oxidizing agent is selected from the group consisting of hydrogen peroxide; sodium periodate; sodium peroxide; urea peroxide; sodium perborate; sodium percarbonate; sodium perphosphate; sodium persilicate; sodium persulphate; and mixtures thereof.

55. A method according to claim 54, wherein the coloration is developed at acidic, neutral, or alkaline pH by employing an oxidizing agent which is added to the dye composition to form a mixture that is then applied to said keratin fibers, or which is present in an oxidizing composition which is applied to said keratin fibers simultaneously with said dye composition or sequentially in a separate manner from said dye composition.

56. A multi-compartment device for the oxidative dyeing of keratin fibers or a multi-compartment kit for the oxidative dyeing of keratin fibers, comprising at least a first compartment containing a composition according to claim 3, and at least a second compartment containing an oxidizing composition.

* * * * *